(12) United States Patent  
Min et al.

(10) Patent No.: US 12,201,826 B2  
(45) Date of Patent: Jan. 21, 2025

(54) ELECTRODE ARRAY AND BODY-IMPLANTABLE DEVICE INCLUDING THE SAME

(71) Applicant: TODOC Co., Ltd., Guro-gu (KR)

(72) Inventors: Kyou Sik Min, Gyeonggi-do (KR); Soo Won Shin, Seocho-gu (KR); June Woo Hyun, Gangnam-gu (KR); Sang Woo Kim, Gangnam-gu (KR); Yoon Hee Ha, Seodaemun-gu (KR); Gwang Jin Choi, Geumcheon-gu (KR)

(73) Assignee: TODOC Co., Ltd., Seoul (KR)

( * ) Notice: Subject to any disclaimer, the term of this patent is extended or adjusted under 35 U.S.C. 154(b) by 531 days.

(21) Appl. No.: 17/403,910

(22) Filed: Aug. 17, 2021

(65) Prior Publication Data

US 2022/0054823 A1 Feb. 24, 2022

(30) Foreign Application Priority Data

Aug. 19, 2020 (KR) .................. 10-2020-0104032  
Jun. 23, 2021 (KR) .................. 10-2021-0081373

(51) Int. Cl.
*A61N 1/00* (2006.01)
*A61N 1/05* (2006.01)

(52) U.S. Cl.
CPC .................. *A61N 1/0541* (2013.01)

(58) Field of Classification Search
None
See application file for complete search history.

(56) References Cited

U.S. PATENT DOCUMENTS

| | | | |
|---|---|---|---|
| 2006/0089700 A1 | 4/2006 | Darley | |
| 2018/0178011 A1 | 6/2018 | Carter | |
| 2018/0353289 A1* | 12/2018 | Min | H04R 25/606 |
| 2018/0353753 A1* | 12/2018 | Vetter | A61N 1/0558 |
| 2022/0143419 A1* | 5/2022 | Choi | A61N 5/0625 |
| 2022/0199285 A1* | 6/2022 | Min | A61B 5/24 |

FOREIGN PATENT DOCUMENTS

| | | | | |
|---|---|---|---|---|
| EP | 3386214 | | 10/2018 | |
| EP | 3721936 | | 10/2020 | |
| KR | 10-1903052 | | 10/2018 | |
| KR | 20190049385 | * | 5/2019 | ............... A61N 1/05 |
| KR | 10-2084179 | | 3/2020 | |
| WO | WO 02/078575 | | 10/2002 | |
| WO | WO 2011/075480 | | 6/2011 | |

OTHER PUBLICATIONS

European Search Report and the European Search Opinion Dated Jan. 26, 2022 From the European Patent Office Re. Application No. 21190161.6. (8 Pages).

Request for the Submission of an Opinion Dated Jan. 6, 2023 From the Korean Intellectual Patent Office Re. Application No. 10-2021-0091373 and Its Translation Into English. (14 Pages).

* cited by examiner

*Primary Examiner* — John R Downey
*Assistant Examiner* — Anant A Gupta

(57) ABSTRACT

The embodiment discloses an electrode array including a housing; a plurality of first contact electrodes exposed to an outside of the housing; a plurality of second contact electrodes exposed to the outside of the housing; a first wire group disposed inside the housing and electrically connected to the first contact electrodes; and a second wire group disposed inside the housing and electrically connected to the second contact electrodes, the plurality of first contact electrodes and the first wire group being disposed on different planes within the housing.

9 Claims, 35 Drawing Sheets

(a)

(b)

ELECTRODE ARRAY AND BODY-IMPLANTABLE DEVICE INCLUDING THE SAME

RELATED APPLICATION

This application claims the benefit of priority of Korean Patent Application Nos. 10-2021-0081373 filed on Jun. 23, 2021 and 10-2020-0104032 filed on Aug. 19, 2020, the contents of which are incorporated herein by reference in their entirety.

FIELD AND BACKGROUND OF THE INVENTION

The embodiment relates to an electrode array and a body-implantable device including the same.

Many medical devices have been developed to help people who have lost a specific function congenitally or acquired. As such medical devices, human body implant devices including nerve assist devices have also been developed.

As one of the human body implant devices, a cochlear implant system, which stimulates the auditory nerve of people who have functioning auditory nerves with electricity to help the people sense sound, has been recognized as the most efficient device among the nerve assist devices developed so far, and such cochlear implants are increasing every year.

The cochlear implant system may include an external device provided outside the body and an internal device provided inside the body.

The external device serves to receive sound from outside the human body and convert the received sound into an electrical signal, and includes a microphone (sender), a speech sound processor (language synthesizer), and a transmitting antenna (transmitter). In this case, the microphone and the transmitting antenna may be combined with a headset.

The internal device serves to stimulate the auditory nerve with signals transmitted from the external device, and includes a receiver and an electrode for reception and stimulation.

The cochlear implant system transmits an acoustic sound transmitted from the microphone attached to a part outside the human body to the auditory nerve fibers through the electrode implanted in the cochlear, without passing through the eardrum or the auditory ossicles, by converting physical vibration of the acoustic signal into an electrical signal through processes of amplification, filtering and the like by the external speech sound processor.

However, the conventional electrode has problems in that cost and time increase and yield decreases because a platinum electrode and a wire are manually resistance-welded and silicon molded. In addition, since the electrode and the wire are manually resistance-welded, there is a limitation in increasing the number of electrodes.

SUMMARY OF THE INVENTION

The embodiment may provide an electrode array capable of being easily manufactured and a body-implantable device including the same.

In addition, the embodiment may provide an electrode array having an increased number of electrodes per unit length and a body-implantable device including the same.

The problems to be solved in the embodiment are not limited thereto, and it will be understood that the purposes or effects that can be grasped from the solutions to the problems or embodiments described below are also included.

An electrode structure according to an embodiment includes a contact electrode part including a plurality of contact electrodes, a plurality of first wires, and a plurality of connection wires connecting the plurality of contact electrodes and the plurality of first wires; a pad part including a plurality of pads and a plurality of second wires connected to the plurality of pads; and a connection part including a plurality of third wires connecting the plurality of first wires and a plurality of second wires, and disposed between the contact electrode part and the pad part, the plurality of first wires and the plurality of third wires extending in a first direction.

The plurality of second wires may be bent at a predetermined angle from the plurality of third wires in a second direction perpendicular to the first direction.

The plurality of first to third wires includes a first wire group and a second wire group adjacent to each other, and a distance in the second direction between the first wire group and the second wire group in the connection part may be greater than that in the contact electrode part and the pad part, and the second direction may be perpendicular to the first direction.

The connection part may include a folding part, and the folding part may include a space formed by a pattern in which the first wire group and the second wire group are spaced apart.

The plurality of contact electrodes may be spaced apart from each other in the first direction.

The plurality of connection wires may include a moire pattern.

The plurality of contact electrodes, the plurality of first wires, the plurality of connection wires, the pad, the plurality of second wires, and the plurality of third wires may be integrally formed.

The electrode array according to an embodiment includes the electrode structure; a first housing including a first groove extending in the first direction; a second housing extending from the first housing and having a second groove; and a cover layer covering the first groove and the second groove and having a plurality of electrode holes. The electrode structure is folded around the folding part so that the contact electrode part and the connection part are disposed in the first groove, the pad part is disposed in the second groove, the plurality of contact electrodes and the plurality of first wires overlap each other with an insulation layer therebetween, and each of the plurality of electrode holes exposes each of the plurality of contact electrodes.

A thickness of the first housing in a third direction may be inversely proportional to a distance from the second housing, and the third direction may be perpendicular to the first direction and the second direction.

A thickness of the first housing in the second direction may be inversely proportional to the distance from the second housing.

The first housing, the second housing, and the cover layer may be integrally formed.

An electrode array according to another embodiment includes the electrode structure; the first housing including the first groove extending in the first direction; the second housing extending from the first housing and having the second groove; the cover layer covering the first groove and the second groove and having the plurality of electrode holes; and an insulation layer surrounding the electrode structure and exposing the contact electrode. The electrode structure is alternately folded in-folding and out-folding based on a first line to an n−1-th line, the contact electrode part and the connection part are disposed in the first groove, the pad part is disposed in the second groove, each of the plurality of electrode holes exposes each of the plurality of contact electrodes, and the first line to the n−1-th line divide the electrode structure into n (n is an integer greater than or equal to 2) regions along the second direction, each region extending in the first direction.

An electrode array according to still another embodiment includes the electrode structure; and the insulation layer surrounding the electrode structure and exposing the contact electrode. The electrode structure is folded in a direction in which the contact electrode is exposed around a reference line dividing the electrode structure in the second direction. In the folded electrode structure, the contact electrode is exposed on an outer circumferential surface, and the folded electrode structure is bent in a cylindrical shape supported by a core bundle disposed therein. The second direction is perpendicular to the first direction.

The core bundle may include a coil spring.

The plurality of third wires may include a moire pattern.

An electrode array according to still another embodiment includes a first electrode structure; and a second electrode structure disposed on the first electrode structure. The first electrode structure includes a first contact electrode part including a plurality of first contact electrodes, a plurality of first-1 wires, and a plurality of first connection wires connecting the plurality of first contact electrodes and the plurality of first-1 wires; a first pad part including a plurality of first pads and a plurality of second-1 wires connected to the plurality of first pads; and a first connection part including a plurality of third-1 wires connecting the plurality of first-1 wires and the plurality of second-1 wires and disposed between the first contact electrode part and the first pad part. The plurality of first-1 wires and the plurality of third-1 wires are extending in a first direction. The second electrode structure includes a second contact electrode part including a plurality of second contact electrodes, a plurality of first-2 wires, and a plurality of second connection wires connecting the plurality of second contact electrodes and the plurality of first-2 wires, a second pad part including a plurality of second pads and a plurality of second-2 wires connected to the plurality of second pads, and a second connection part including a plurality of third-2 wires connecting the plurality of first-2 wires and the plurality of second-2 wires and disposed between the second contact electrode part and the second pad part. The plurality of first-2 wires and the plurality of third-2 wires are extending in the first direction. The first contact electrode part is folded around a reference line dividing the first contact part in the second direction, and the second contact electrode part is folded around a reference line dividing the second contact part in the second direction.

The plurality of first contact electrodes of the first electrode structure and the plurality of second contact electrodes of the second electrode structure may be disposed to be deviated in a vertical direction.

A first housing including a first groove extending in the first direction; a second housing extending from the first housing and having a second groove; a cover layer covering the first groove and the second groove and having a plurality of electrode holes; an insulation layer surrounding the first electrode structure and exposing the first contact electrode; and an insulation layer surrounding the second electrode structure and exposing the second contact electrode are included. The first contact electrode part, the first connection part, the second contact electrode part, and the second connection part may be disposed in the first groove, and the first pad part and the second pad part may be disposed in the second groove.

The plurality of third-1 wires and the plurality of third-2 wires at least partially overlap in the third direction. In the first groove, the plurality of first contact electrodes and the plurality of second contact electrodes may be adjacent to each other in the first direction and may not overlap each other in the third direction.

The plurality of third-1 wires and the plurality of third-2 wires may include a moire pattern.

According to an embodiment, since an electrode structure is manufactured by patterning an electrode and a wire using a laser, and an electrode array is formed by folding the electrode structure, ease of manufacture may be improved.

In addition, the number of electrodes disposed per unit length increases.

Various and advantageous benefits and effects of embodiments are not limited to the above, and will be more easily understood in the course of describing specific embodiments of the present invention.

BRIEF DESCRIPTION OF THE SEVERAL VIEWS OF THE DRAWINGS

FIG. 18b is a front view of FIG. 18a.

DESCRIPTION OF SPECIFIC EMBODIMENTS OF THE INVENTION

Figure 1:
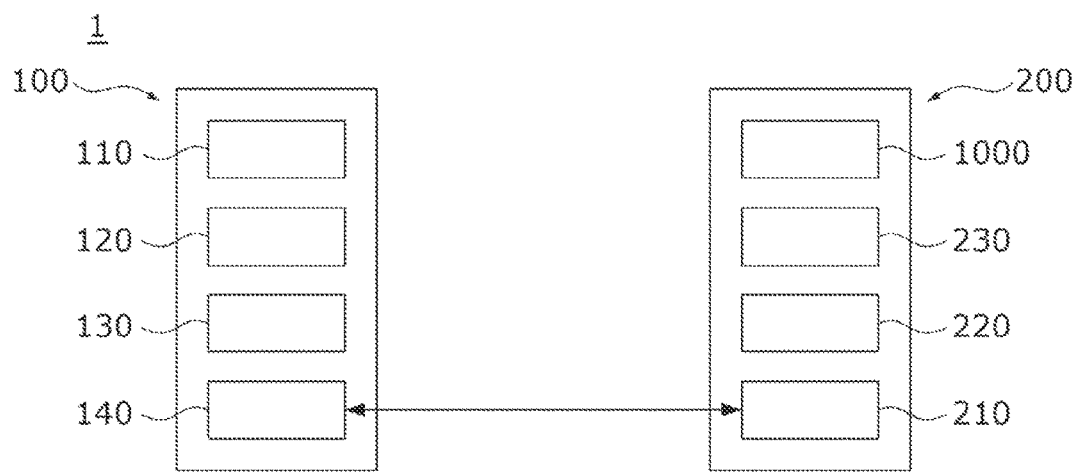
FIG. 1 is a conceptual view of an implantable device according to an embodiment.

Since the present invention can have various changes and various embodiments, specific embodiments are illustrated and described in the drawings. However, this is not intended to limit the present invention to specific embodiments, and it should be understood that all modifications, equivalents and substitutes included in the spirit and scope of the present invention are included.

Terms including an ordinal number such as second, first, etc. may be used to describe various elements, but the elements are not limited by the terms. The above terms are used only for the purpose of distinguishing one component from another component. For example, without departing from the scope of the present invention, a second component may be referred to as a first component, and similarly, a first component may also be referred to as a second component. The term and/or includes a combination of a plurality of related listed items or any of a plurality of related listed items.

When a component is referred to as being "connected" or "contacted" to another component, it should be understood that the other component may be directly connected or contacted to the other component, but other components may exist in between them. On the other hand, when it is mentioned that a certain element is "directly connected" or "directly contacted" to another element, it should be understood that no other element is present in the middle.

The terms used in the present application are only used to describe specific embodiments, and are not intended to limit the present invention. The singular expression includes the plural expression unless the context clearly dictates otherwise. In the present application, terms such as "comprise" or "have" are intended to designate the existence of a feature, number, step, operation, component, part, or combination thereof described in the specification, but it should be understood that this does not preclude the possibility of the presence or addition of one or more of other features, numbers, steps, operations, components, parts, or combinations thereof.

Unless defined otherwise, all terms used herein, including technical or scientific terms, have the same meaning as commonly understood by one of ordinary skill in the art to which this invention belongs. Terms such as those defined in a commonly used dictionary should be interpreted as having a meaning consistent with the meaning in the context of the related art, and should not be interpreted in an ideal or excessively formal meaning unless explicitly defined in the present application.

Hereinafter, embodiments will be described in detail with reference to the accompanying drawings, but the same or corresponding components are given the same reference numerals regardless of reference numerals, and redundant descriptions thereof will be omitted.

Figure 2:
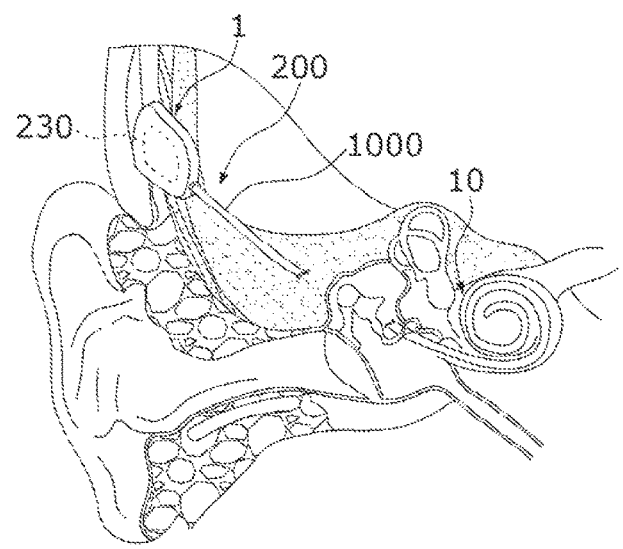
FIG. 2 is an exemplary view showing that a second unit of an implantable device according to an embodiment is applied to a human body.

FIG. 1 is a conceptual view of an implantable device according to an embodiment. FIG. 2 is an exemplary view showing that a second unit of an implantable device according to an embodiment is applied to a human body.

FIGS. 1 and 2, an implantable device 1 according to an embodiment may include a first unit 100 and a second unit 200 that can communicate with each other. Hereinafter, one of the implantable devices, a cochlear implant system, will be described as example. However, the embodiment is not limited thereto. For example, the second unit 200 may be a device that provides electrical signals to other organs or organs of the human body.

The first unit 100 may convert a sound signal into an electrical signal and provide it, and may include a first coil 140 for supplying power. The first unit 100 may be disposed on an outside of a skin. That is, the first unit 100 may be an external device mounted outside a body without being implanted in the body.

The first unit 100 may include a sender 110, a voice processor 120, a transmitter 130, and a first coil 140.

The sender 110 may detect an acoustic signal. The acoustic signal may include a voice signal or a sound signal. Various electronic devices capable of detecting the acoustic signal may be selected for the sender 110. In an embodiment, the sender 110 may be a microphone, but is not limited thereto. The sender 110 may include a volume adjuster that adjusts the volume of the received acoustic signal.

The voice processor 120 may receive the acoustic signal sensed by the sender 110 and convert it into an electrical signal. The voice processor 120 may include a speech processor.

The transmitter 130 may receive the electrical signal from the voice processor 120 and transmit it. The first coil 140 may supply power. However, the present invention is not limited thereto, and the transmitter 130 may be omitted. That is, the first unit 100 may not include a separate transmitter 130. In this case, the first unit 100 may receive the electrical signal from the voice processor 120 and transmit the electrical signal to the second unit 200 while power is being transmitted thereto through the first coil 140.

The first unit 100 may include a power source (not shown). The power source is a configuration for supplying power to the first unit 100 and may include a replaceable battery, a rechargeable battery and the like.

The power source may receive power from an outside and store the power. For example, the power source may include a capacitive element such as a capacitor. The capacitive element may receive power from an external power source via a wire and store it, or wirelessly receive power from an external power source through the first coil 140 of the first unit 100.

For example, in a charging mode, the first coil 140 may receive power wirelessly from the coil of the external power source through electromagnetic induction and store it in the capacitive element, and in a transmission mode, the power of the capacitive element may be wirelessly transmitted to the second coil 210 of the second unit 200.

Here, although the electromagnetic induction phenomenon may be used for transmitting power through the coil, embodiments are not limited thereto, and other wireless power transmission techniques may also be used.

The second unit 200 may be an internal implant inserted inside a skin. In one embodiment, the second unit 200 may be inserted into a subcutaneous fat layer, but is not limited thereto.

The second unit 200 may receive an electrical signal from the first unit 100, and stimulate auditory nerve fibers in a cochlea 10.

The second unit 200 may include a receiver 220, a circuit 230 configured to process a signal received from the first unit 100 to generate a stimulation signal, and an electrode array 1000 having a plurality of electrodes (not shown) configured to stimulate the auditory nerve fibers in the cochlea 10 with a current signal in response to the stimulation signal transmitted from the circuit 230.

The receiver 220 may receive a signal from the first unit 100. For example, the receiver 220 may include the second coil 210 that receives a signal along with power through the first coil 140. When transmitting power, the first coil 140 of the first unit 100 may transmit a data signal for electrical stimulation together with the power signal. For example, the first coil 140 may vary the amplitude or phase of the power signal and transmit the data signal along with the power signal.

Alternatively, the receiver 220 may directly receive a signal from the transmitter 130 of the first unit 100. The transmitter 130 and the receiver 220 may communicate using various communication techniques that are not limited to a specific communication technique. In addition, the data signal may be communicated separately from the power signal through a separate communication means or a separate frequency not described above.

The circuit 230 may generate a stimulation signal by processing the electrical signal received from the receiver 220. The circuit 230 may have an integrated circuit (IC) for generating the stimulation signal. The circuit 230 may perform various functions necessary for the normal operation of the implantable device 1, such as signal processing, communication and the like, and be composed of one or more functional modules.

Also, the circuit 230 may include a terminal electrically connected to one end of the electrode array 1000, and a signal (e.g., current, voltage, etc.) may be provided to the circuit 230 or the electrode array 1000 through the terminal.

The electrode array 1000 may have a structure in which a plurality of electrodes (not shown) is disposed on an insulation layer. The electrode array 1000 may be thinly formed to be inserted into the cochlea 10 of a human body. The electrode array 1000 may transmit the stimulation signal generated from the circuit 230 to the cochlea 10, and the stimulation signal may stimulate the auditory nerve of the cochlea 10. The user of the body-implantable device 1 may sense an external sound through stimulation of the auditory nerve.

Figure 3:
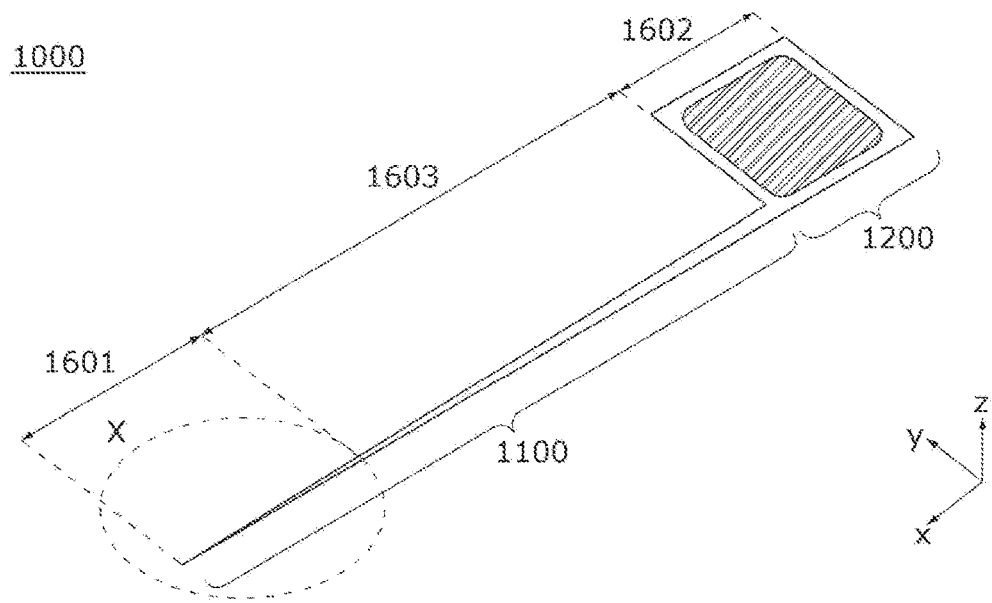
FIG. 3 is a view showing an electrode array according to a first embodiment.
Figure 4:
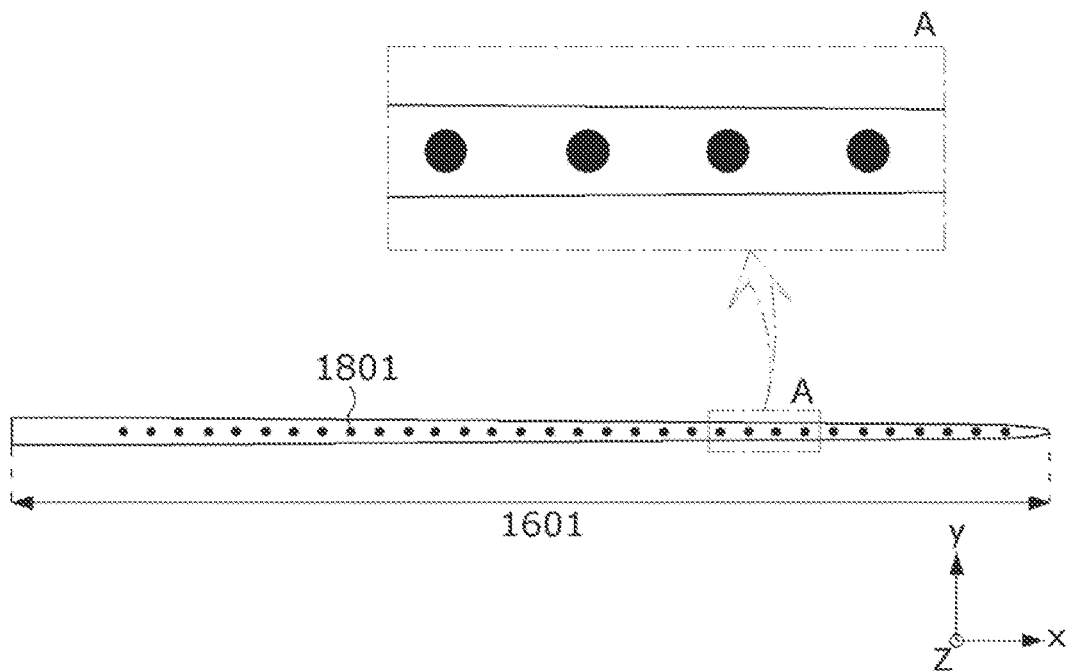
FIG. 4 is an enlarged view of X in FIG. 3.
Figure 5:
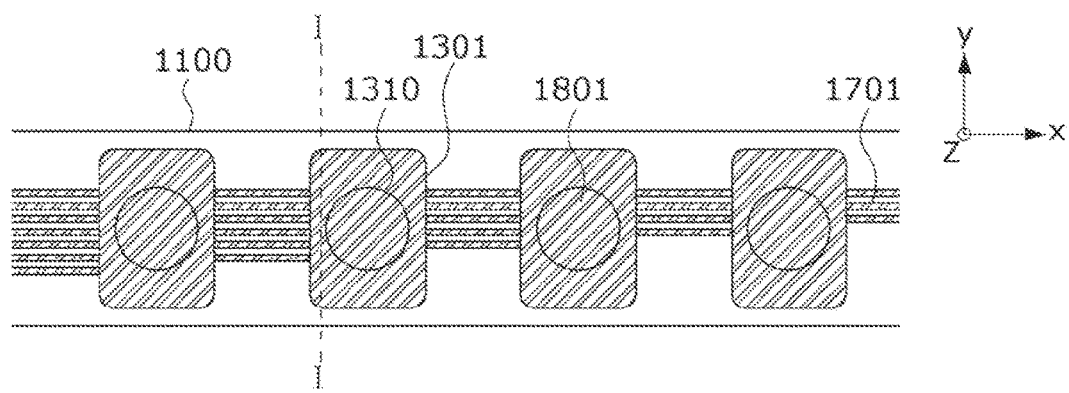
FIG. 5 is an enlarged view of A in FIG. 4.
Figure 6:
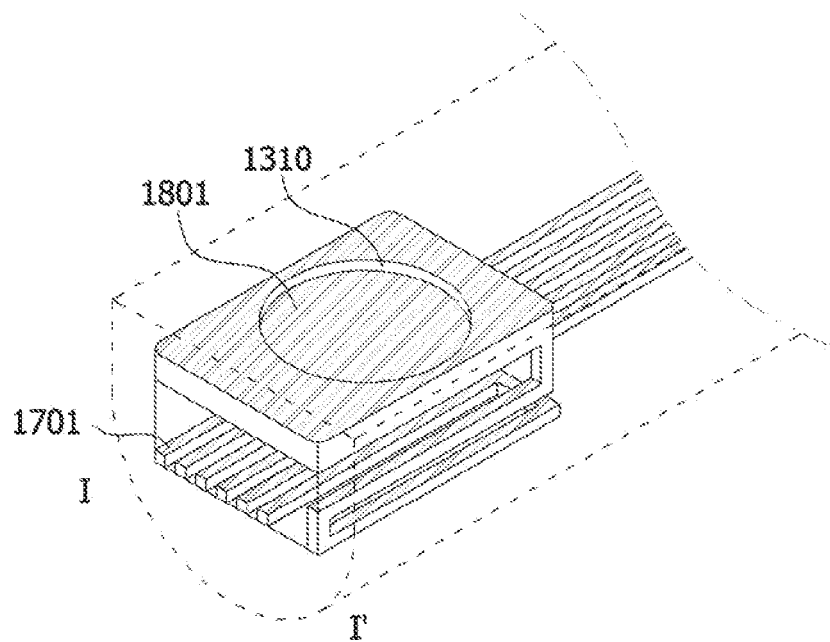
FIG. 6 is a view taken along line I-I' in FIG. 5.
Figure 6:
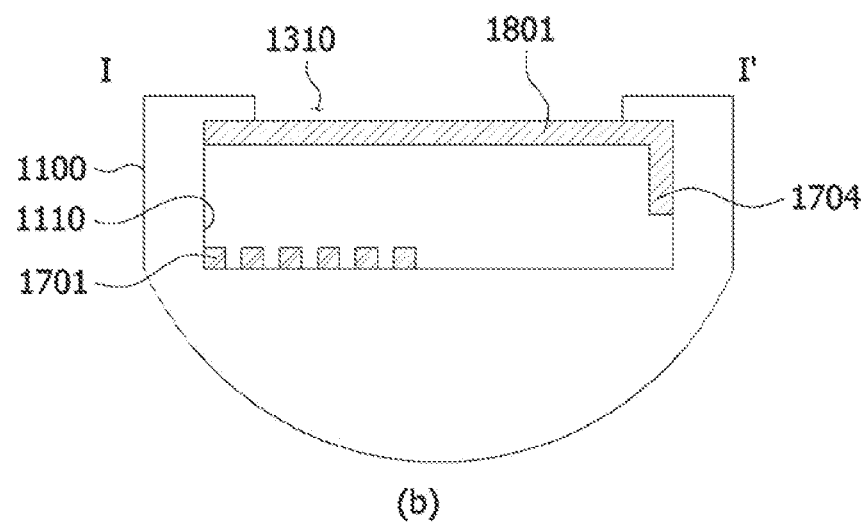
Figure 7:
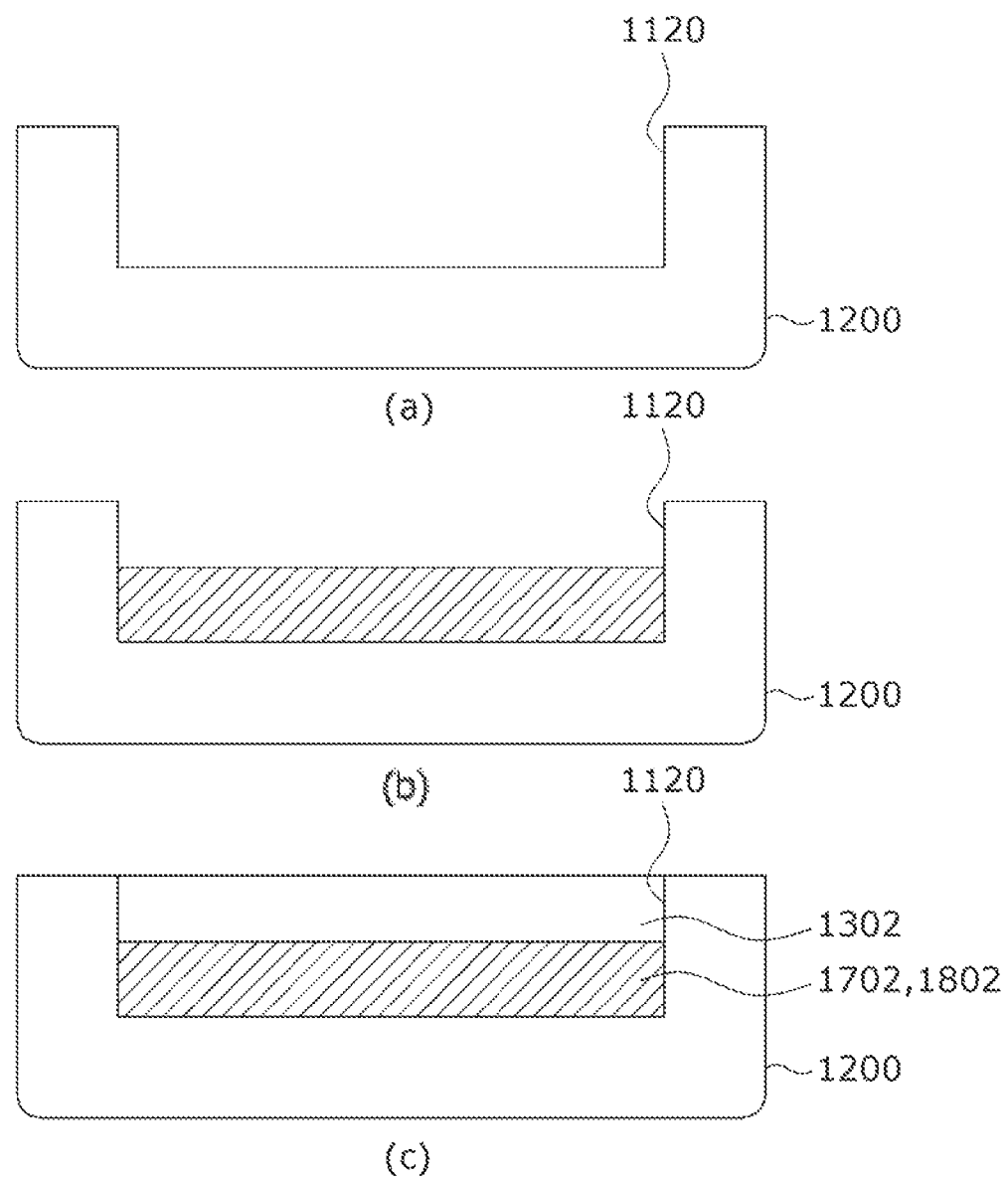
FIG. 7 is a schematic view showing a cross-section of a pad part in FIG. 3.
Figure 8:
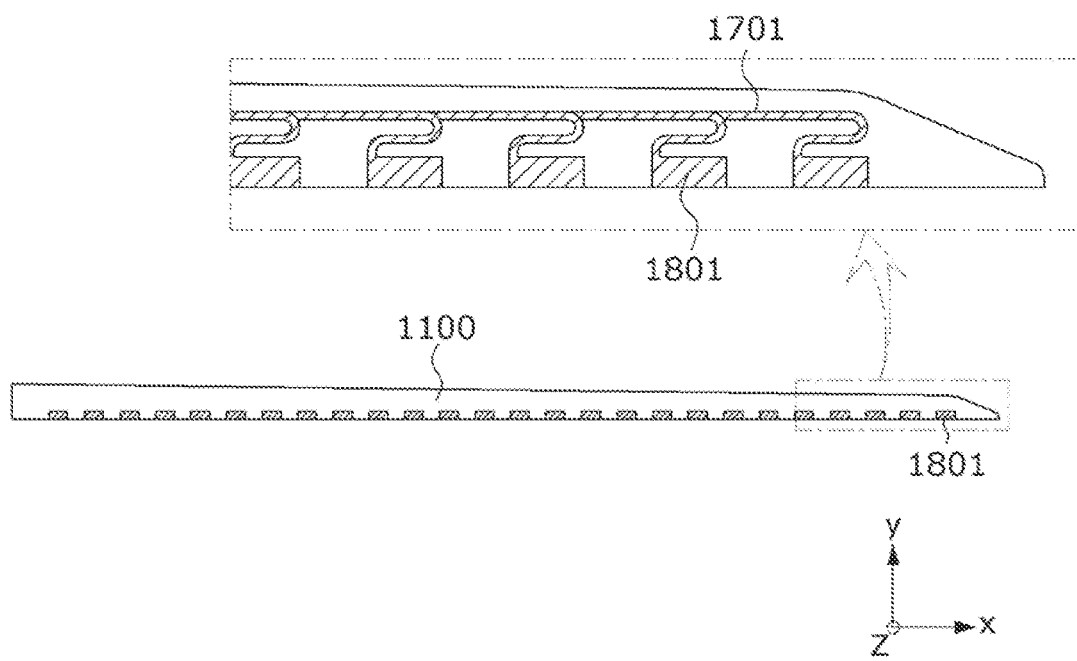
FIG. 8 is a view viewed from a side of FIG. 4.

FIG. 3 is a view showing an electrode array according to an embodiment. FIG. 4 is an enlarged view of X in FIG. 3. FIG. 5 is an enlarged view of A in FIG. 4. FIG. 6 is a view taken along line I-I' in FIG. 5. FIG. 7 is a schematic view showing a cross-section of a pad part in FIG. 3. FIG. 8 is a view viewed from a side of FIG. 4.

Hereinafter, an electrode array according to an embodiment will be described with reference to FIGS. 3 to 8.

Referring to FIG. 3, the electrode array 1000 according to an embodiment includes a first housing 1100, a second housing 1200, and an electrode structure (not shown) disposed in the first housing 1100 and the second housing 1200. Hereinafter, the overall configuration of the electrode array 1000 will be described, and a detailed description of the electrode structure will be described later.

Referring to FIGS. 3 to 6, a plurality of wires 1701, 1703, and 1704 and a plurality of contact electrodes 1801 may be disposed in the first housing 1100. More specifically, the first housing 1100 may include a first groove 1110. The plurality of wires 1701, 1703, and 1704, and the plurality of contact electrodes 1801 may be disposed in the first groove 1110.

The contact electrodes 1801 may be exposed to an outside of the electrode array. More specifically, the first housing 1100 may include a first cover layer 1301 to cover the first wire 1701, the third wire 1703, the connection wire 1704, and the contact electrodes 1801 disposed on the first groove 1110. The first cover layer 1301 may include a plurality of electrode holes 1310 to expose at least a portion of the plurality of contact electrodes 1801. In one embodiment, the plurality of electrode holes 1310 may be matched one-to-one with the plurality of contact electrodes 1801 to expose one first electrode 1801 per one electrode hole 1310, but the embodiment is not limited thereto.

The electrode hole 1310 may serve as an inlet for a biometric signal to be collected when the body-implantable device 1 collects the biometric signal, and an outlet for a biometric stimulation signal when the body-implantable device 1 transmits the biometric stimulation signal to a body. There may be a plurality of such electrode holes 1310, and the number may be the same as the number of terminals of the circuit 230, but the embodiment is not limited thereto. Also, as described above, the number of electrode holes 1310 may be the same as the number of contact electrodes 1801, but the embodiment is not limited thereto. The number of electrode holes 1310 may be appropriately adjusted as necessary.

When the body-implantable device 1 is inserted into the cochlea, the plurality of exposed contact electrodes 1801 may contact auditory nerve fibers. The contact electrode 1801 in contact with the auditory nerve fibers may transmit an external signal to the auditory nerve fibers or, conversely, may transmit a signal from the auditory nerve fibers to an outside. However, this is only an example, and as described above, the body-implantable device according to the embodiment may be implanted and used in other body organs. Since the plurality of contact electrodes 1801 is in contact with a body, they may be made of a material that is not harmful to the body. For example, the plurality of contact electrodes 1801 may include platinum iridium (ptIr), but is not limited thereto.

In FIG. 7, (a) is a view showing a second housing, (b) is a view showing a plurality of second wires and a plurality of pads disposed in a second groove of the second housing, (c) is a view showing a cover layer covering the second housing.

Referring to FIG. 7, a plurality of second wires 1702 and a plurality of pads 1802 may be disposed in the second housing 1200. More specifically, the second housing 1200 may include a second groove 1120. The plurality of second wires 1702 and the plurality of pads 1802 may be disposed in the second groove 1120. A second cover layer 1302 may be disposed on the second groove 1120 in which the plurality of second wires 1702 and the plurality of pads 1802 are disposed. That is, the second cover layer 1302 may cover the second groove 1120.

The second cover layer 1302 may be disposed on the second groove 1120 of the second housing 1200 and cover all or part of the pad 1802 disposed inside the second groove. The pad 1802 may be connected to the circuit 230 disposed on the second housing 1200. There is no limitation in the manner in which the pad 1802 and the circuit 230 are connected. In one embodiment, a contact hole may be formed in the second housing 1200, and the pad and the circuit may be connected using this or a feed-through.

The circuit 230 transmits an electrical signal to the pad 1802 connected to the circuit, and the pad 1802 may transmit the electrical signal to the auditory nerve fibers through the second wire 1702, the third wire 1703, the first wire 1701, the connection wire 1704, the contact electrode 1801 that are sequentially connected. In addition, in a reverse mechanism, the biometric signal may be transmitted to the circuit 230 through the contact electrode 1801, the connection wire 1704, the first wire 1701, the third wire 1703, the second wire 1702, and the pad 1802. Such an electrical signal may be an electrical signal necessary for the operation of the implantable device 1.

The first housing 1100, the second housing 1200, and the cover layers 1301 and 1302 may be integrally formed. That is, the first housing 1100, the second housing 1200, and the cover layers 1301 and 1302 may include the same insulation material. In addition, since the first housing 1100, the second housing 1200, and the cover layers 1301 and 1302 may come into contact with a body, they may be made of a material not harmful to the body.

For example, the insulation material may include a silicone elastomer. The insulation material can prevent an unwanted short from occurring between the respective components of the contact electrode 1801, the pad 1802, and the wires 1701, 1702, 1703, and 1704, and block the inflow of an electrical signal from an outside.

As one embodiment, referring to FIGS. 6 and 7, the insulation material may be disposed between the contact electrode 1801 and the first wire 1701 to serve as an insulation layer. That is, the inside of the first groove 1110 in FIGS. 6 and 7 may be filled with the insulation material. Similarly, the inside of the second groove 1120 may be filled with the insulation material. At the same time, the insulation material may play a role of the housing 1100, 1200, which surrounds the contact electrode 1801, the pad 1802, the first to third wires 1701, 1702, 1703, and the connection wire 1704 to block the inflow of unnecessary electrical signals from an outside.

Referring to FIGS. 3, 4, and 8, the thickness of the electrode array 1000 according to the embodiment may become smaller as it is farther from the second housing 1200. The thickness is a length in a third direction, that is, a z-direction. More specifically, according to the embodiment, a size in the third direction of the first housing 1100 may be inversely proportional to a distance from the second housing 1200. In other words, the thickness of the first housing 1100 positioned farther from the second housing 1200 in the first direction may gradually decrease. However, the embodiment is not limited thereto, and the thickness of the first housing 1100 in the first direction may be the same.

In addition, according to the embodiment, the width of the electrode array 1000 may become smaller as it is farther from the second housing. The width is a length in a second direction, that is, a y-direction. More specifically, the size in the second direction of the first housing 1100 according to the embodiment may be inversely proportional to a distance from the second housing 1200. In other words, the width of the first housing 1100 located farther from the second housing 1200 in the first direction may gradually decrease. However, the embodiment is not limited thereto, and the width of the first housing 1100 in the first direction may be the same.

The reason why the width and thickness of the first housing 1100 are inversely proportional to the distance from the second housing 1200 will be described with reference to FIGS. 2 and 9.

Figure 9:
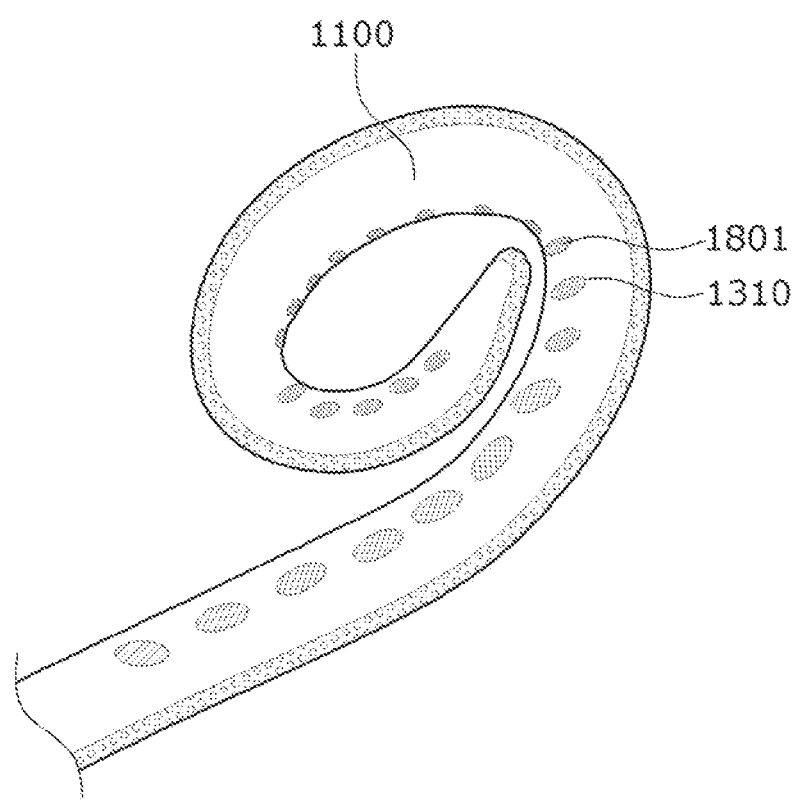
FIG. 9 is an enlarged view of a contact electrode part disposed inside a cochlea in FIG. 2.

FIG. 9 is an enlarged view of a contact electrode disposed inside a cochlea in FIG. 2.

Referring to FIGS. 2 and 9, when the electrode array according to the embodiment is implanted in a body, it may be bent to be implanted so as to be properly connected to a nerve according to a body organ. For example, in order for the body-implantable device 1 according to the embodiment to be implanted in the cochlea 10, it is necessary to be bent according to the shape of the cochlea 10 for implanting. Therefore, it may be advantageous for the first housing 1100 in which the electrode to be connected to the body is positioned to have flexibility.

In order to increase the flexibility of the electrode array 1000 according to the embodiment, a flexible material may be used. In addition, if the width and thickness of the first housing 1100 are formed to be inversely proportional to the distance from the second housing 1200, the flexibility of the electrode array 1000 may be further increased.

Hereinafter, a basic shape and structure of an electrode structure disposed inside an electrode array according to an embodiment will be described with reference to FIGS. 10 to 13.

Figure 10:
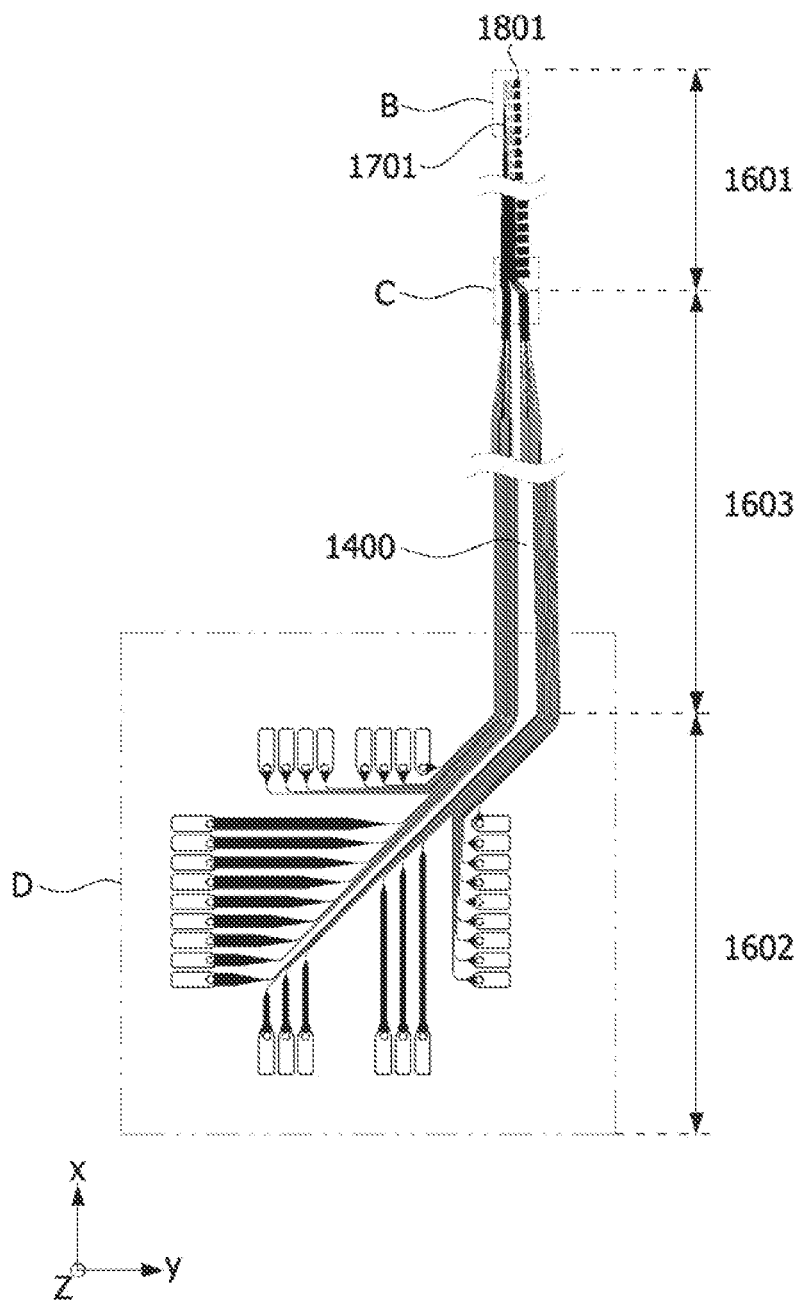
FIG. 10 is a view showing an electrode structure according to an embodiment.
Figure 11:
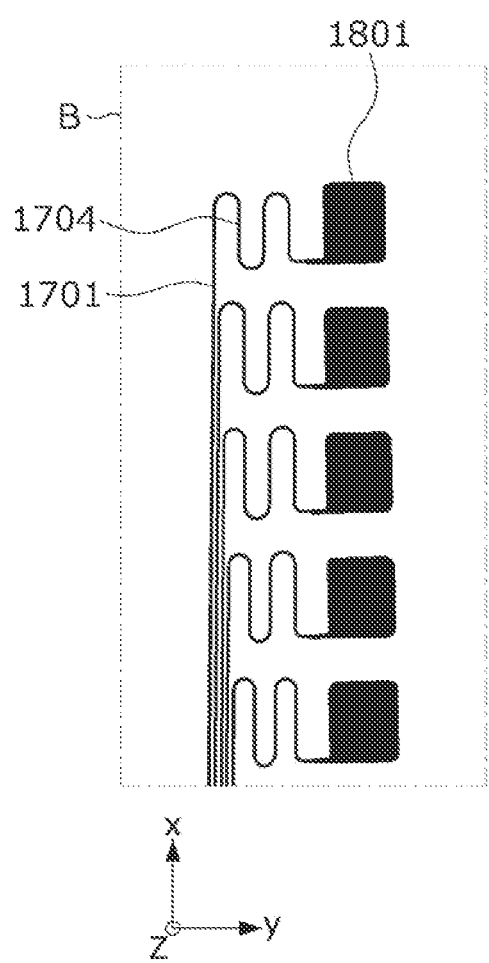
FIG. 11 is an enlarged view of B in FIG. 10.
Figure 12:
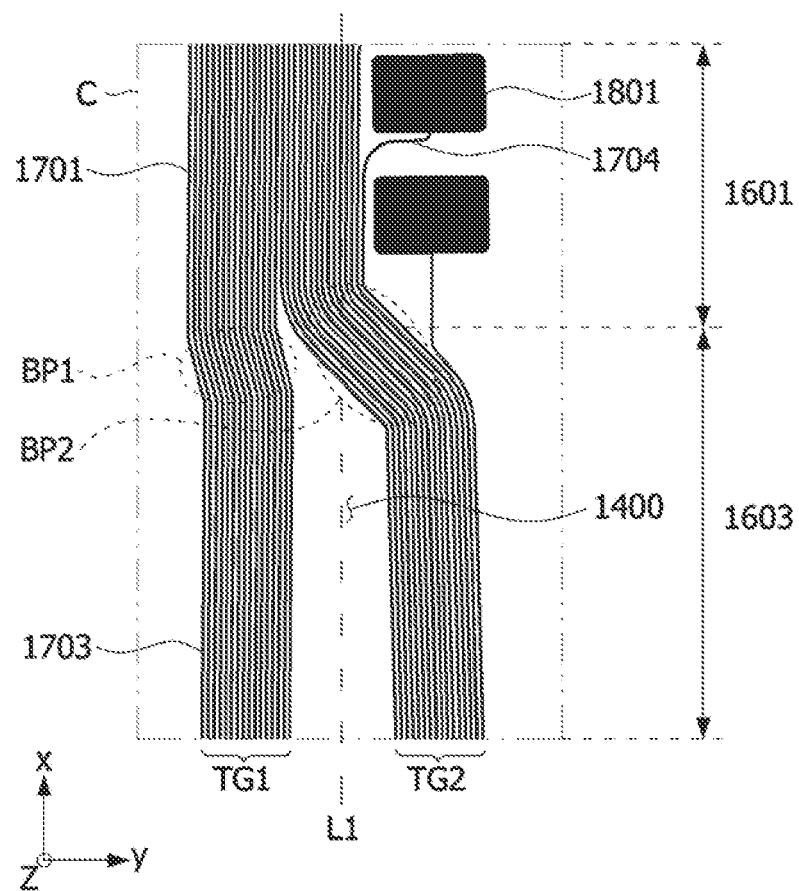
FIG. 12 is an enlarged view of C in FIG. 10.
Figure 13:
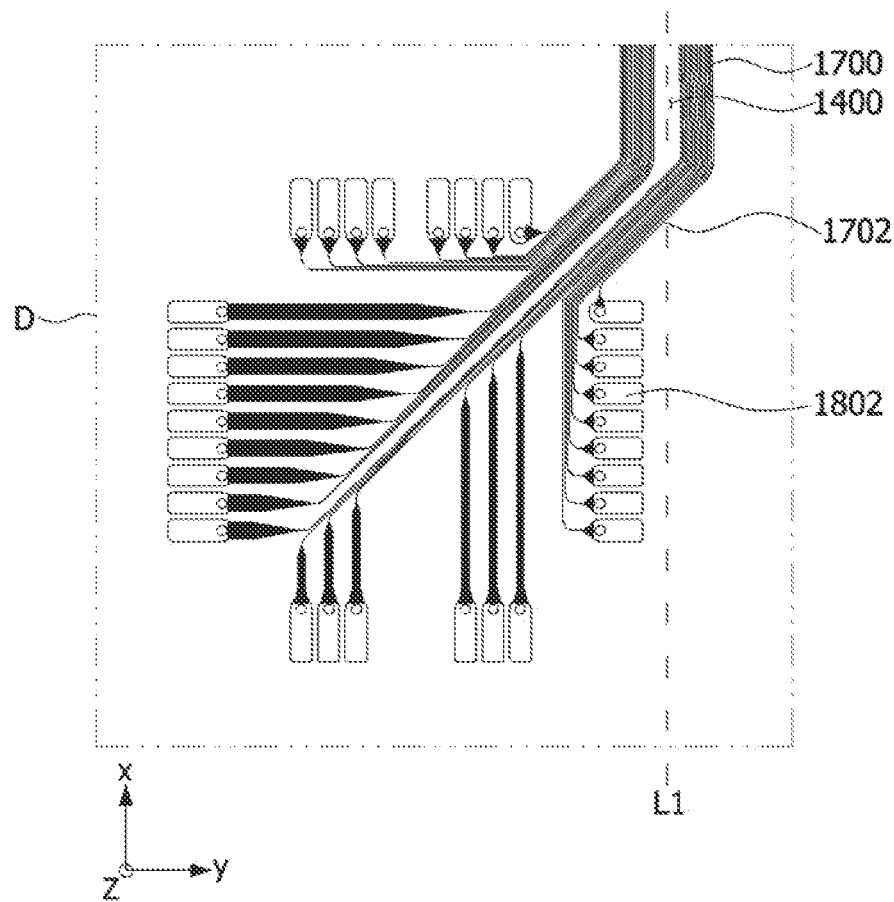
FIG. 13 is an enlarged view of D in FIG. 10.

FIG. 10 is a view showing an electrode structure according to an embodiment. FIG. 11 is an enlarged view of part B in FIG. 10. FIG. 12 is an enlarged view of part C in FIG. 10. FIG. 13 is an enlarged view of part D in FIG. 10.

Referring to FIGS. 10 to 13, an electrode structure 1500 according to an embodiment may include a contact electrode part 1601, a pad part 1602, and a connection part 1603.

The contact electrode part 1601 may be a region in which the plurality of contact electrodes 1801, the plurality of first wires 1701, and the plurality of connection wires 1704 are disposed. The pad part 1602 may be a region in which the plurality of pads 1802 and the second wire 1702 are disposed. The connection part 1603 may be a region in which the plurality of third wires 1703 are disposed and a folding part 1400 is positioned.

The contact electrode 1801, the pad 1802, the first wire 1701, the second wire 1702, the third wire 1703, and the connection wire 1704 may form an integral body. In other words, the contact electrode 1801, the pad 1802, the first wire 1701, the second wire 1702, the third wire 1703, and the connection wire 1704 may all be connected.

That is, the contact electrode 1801 is connected to the connection wire 1704, the connection wire 1704 is connected to the first wire 1701, the first wire 1701 is connected to the third wire 1703, the third wire 1703 is connected to the second wire 1702, and the second wire 1702 is connected to the pad 1802, so that they may be integrally formed.

Since the contact electrode 1801, the pad 1802, the first wire 1701, the second wire 1702, the third wire 1703, and the connection wire 1704 are integrally formed, they may be made of the same material. For example, the contact electrode 1801, the pad 1802, the first wire 1701, the second wire 1702, the third wire 1703, and the connection wire 1704 may include a conductive material, in one embodiment, the conductive material may include platinum iridium (PtIr).

The folding part 1400 may be positioned in the connection part 1603 and may be a reference region for folding the electrode structure 1500. As one embodiment, the folding part 1400 may be a space extending in the first direction, that is, in the longitudinal direction, after passing through the center of the connection part 1603. However, the embodiment is not limited thereto, and the folding part 1400 may not pass through the center of the connection part 1603.

The folding part 1400 may be appropriately changed and formed to include a portion that needs to be folded. For example, when the electrode structure 1500 needs to be folded twice or more, the electrode structure 1500 may include two or more folding parts 1400.

In this case, each folding part 1400 may be formed to include a section to be folded, respectively. In the manufacturing process of the electrode array 1000 according to the embodiment, the electrode structure 1500 may be folded and disposed in the housings 1100 and 1200, and the folding part 1400 may a space formed to facilitate folding in the corresponding process.

The contact electrode part 1601 and the connection part 1603 may be disposed in the first housing 1100, and the pad part 1602 may be disposed in the second housing 1200.

Referring to FIG. 11, the contact electrode 1801, the first wire 1701, and the connection wire 1704 may be disposed in the contact electrode part 1601. In one embodiment, the contact electrode 1801 may be matched one-to-one with the first wire 1701. That is, one contact electrode may be connected to one wire. However, the embodiment is not limited thereto.

More specifically, the first wire 1701 and the contact electrode 1801 may be connected through the connection wire 1704. The connection wire 1704 may be a wire formed to face the second direction from the end of the first wire 1701 extending in the first direction to connect the contact electrode 1801 and the first wire 1701. That is, the electrode structure 1500 according to the embodiment may include the connection wire 1704 that connects the first wire 1701 and the contact electrode 1801 and is bent from the first wire 1701 in the second direction.

As described above, the first wire 1701, the connection wire 1704, and the contact electrode 1801 may form an integral structure as one structure connected to each other.

When the electrode structure 1500 is folded around the folding part 1400 to form the electrode array 1000, all or part of the connection wire 1704 may be folded. The contact electrode part 1601 may be folded around the connection wire 1704 so that the contact electrode 1801 and the first wire 1701 are disposed to face each other. An insulation layer may be disposed between the opposing contact electrode 1801 and the first wire 1701. The insulation layer may include an insulation material such as the silicone elastomer described above.

The connection wire 1704 may have various structures for facilitating folding. In one embodiment, the connection wire 1704 may include a zigzag pattern. In another embodiment, the connection wire 1704 may include a concave-convex pattern. In still another embodiment, the connection wire 1704 may include a moire pattern. When the connection wire 1704 includes such a pattern, the amount of tension applied to the corresponding wire during bending can be reduced compared to that of a straight wire, so that flexibility can be increased. If the flexibility of the wire is improved, the risk of wire short due to the tension applied during bending is reduced, so that stability can be provided to the device. However, any various structures capable of increasing flexibility may be applied to the connection wire 1704, and the embodiment is not limited to a zigzag pattern, a concave-convex pattern, or a moire pattern. Also, the connection wire 1704 may have a straight shape.

Referring to FIG. 12, the third wire 1703 and the folding part 1400 may be positioned in the connection part 1603.

As described above, the folding part 1400 may be a space formed to easily facilitate the folding of the electrode structure 1500 and may be a space through which a wire does not pass.

In order to form the folding part 1400, the first and third wires 1701 and 1703 positioned in the region where the contact electrode part 1601 and the connection part 1603 are connected may have bent patterns BP1 and BP2 in some regions.

In other words, the first wire 1701 and the third wire 1703 may include a bent pattern at a predetermined angle at a place where the two wires are connected to each other, and the space formed by the bent pattern may be the folding part 1400. For forming the folding part 1400, the first wire 1701 and the third wire 1703 may be bent a plurality of times.

The third wire 1703 may include a first wire group TG1 and a second wire group TG2 partitioned by a virtual line L1 passing through the center of the folding part 1400, and the first wire group TG1 and the second wire group TG2 may have bent patterns BP1 and BP2, respectively. However, the embodiment is not limited thereto, and the bent pattern may be formed only in one of the first wire group TG1 and the second wire group TG2.

From another point of view, the wires 1701, 1702, and 1703 may include a pattern bypassing the folding part 1400. That is, a space in which the wires 1701, 1702, and 1703 arranged at regular intervals in the second direction move away in the second direction and return to the original interval in the third electrode unit 1603 may be the folding part 1400.

More specifically, the interval between the first wire group TG1 and the second wire group TG2 may be different in the contact electrode part 1601, in the connection part 1603, and in the pad part 1602. The interval between the first wire group TG1 and the second wire group TG2 in the connection part 1603 may be greater than that in the contact electrode part 1601 and the pad part 1602. The folding part 1400 may include a space formed by a pattern spaced apart by a predetermined distance formed by the first wire group TG1 and the second wire group TG2 in the connection part 1603.

Referring to FIG. 13, the pad part 1602 may include the plurality of second wires 1702 and the plurality of pads 1802. The second wire 1702 is a wire extending from the third wire 1703 and may have a pattern bent at a predetermined angle in the second direction in a region where the two wires are connected. That is, the plurality of pads 1802 may be disposed on one side of the virtual line L1.

This is to prevent the pads 1802 from overlapping each other in the third direction when the electrode array 1000 is formed by folding the electrode structure 1500. The pads 1802 are configured to be connected to respective terminals of the circuit 230 disposed on the second housing, and thus they should not overlap each other in the third direction. The bending angle may be appropriately adjusted for each specific shape of the electrode structure 1500. For example, as in the case of the embodiment shown in FIG. 24, in the case of the electrode structure 1500 that does not interfere with being connected to the circuit 230 even when the pad 1802 and the second wire 1702 partially overlap, the bending angle may be smaller than that in the embodiment of FIG. 13. Also, even if the pads 1802 overlap in the third direction, it may not be bent if there is no problem in its connection according to a specific design of the circuit 230.

The pad 1802 and the second wire 1702 may be matched one-to-one. The second wire 1702 and the third wire 1703 may also be matched one-to-one. However, the embodiment is not limited thereto, and may be matched one-to-many. As described above, the pad 1802, the second wire 1702, and the third wire 1703 may form an integral body. That is, it may be one configuration.

As described above, the pads 1802 may be connected to the electrodes of the circuit 230 through a contact hole formed in the second housing 1200 or using a feed-through. Here, the electrodes of the circuit 230 may constitute individual channels. Accordingly, each of the contact electrodes 1801 extending from the pads 1802 may form an independent channel, and the number of contact electrodes 1801 and the number of pads 1802 may correspond to the number of channels, but the embodiment is not limited thereto.

Hereinafter, a method of manufacturing the electrode array 1000 according to an embodiment will be described with reference to FIGS. 14 to 25.

Figure 14:
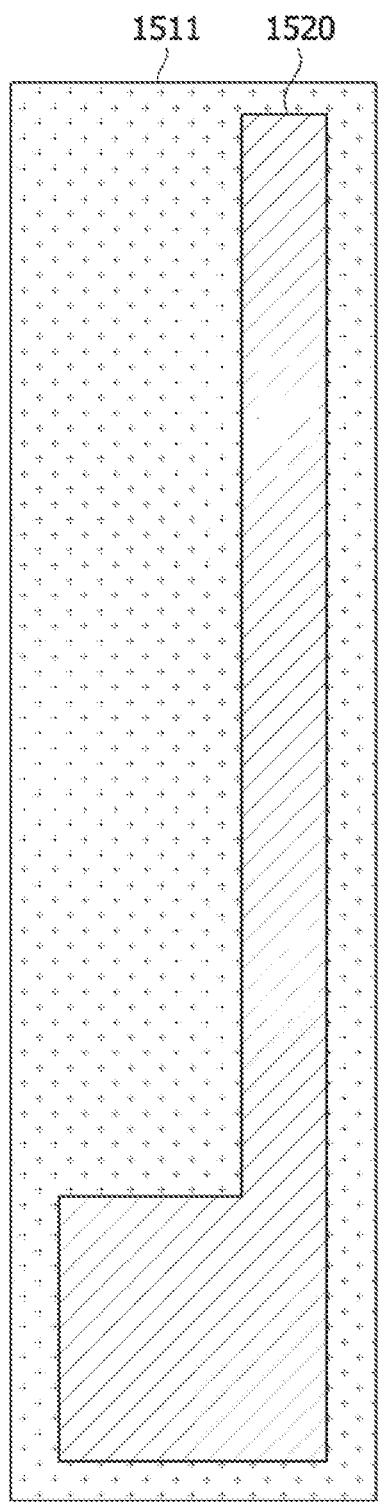
FIG. 14 is a plan view showing a substrate and a conductive material disposed on the substrate.
Figure 15:
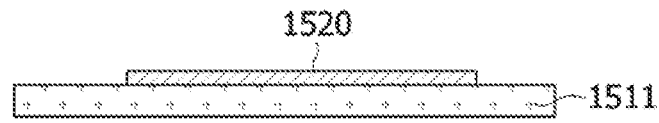
FIG. 15 is a cross-sectional view showing a substrate and a conductive material disposed on the substrate.

FIG. 14 is a plan view showing a substrate and a conductive material disposed on the substrate. FIG. 15 is a cross-sectional view showing a substrate and a conductive material disposed on the substrate.

First, a patterning preparation step will be described. Referring to FIGS. 14 and 15, the patterning preparation step is a step of forming a conductive material 1520 on a substrate 1511. In one embodiment, the substrate 1511 may be a self-adhesive film, and the conductive material may be a platinum iridium foil (PtIr foil). However, the embodiment is not limited thereto, any material that can be used in the patterning process may be used as the substrate 1511, and any material having conductivity that is easy to be patterned and harmless to a human body may be used as the conductive material 1520.

Figure 16:
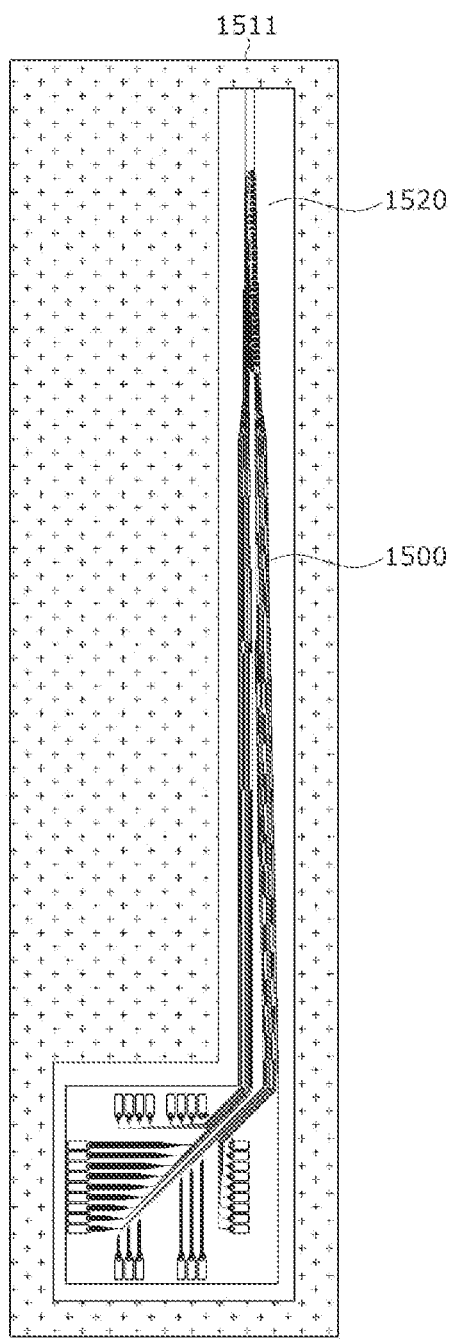
FIG. 16 is a view showing a process of forming an electrode structure by patterning a conductive material disposed on a substrate.
Figure 17:
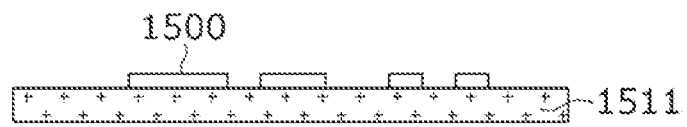
FIG. 17 is a cross-sectional view showing a process of forming an electrode structure by patterning a conductive material disposed on a substrate.

FIG. 16 is a view showing a process of forming an electrode structure by patterning a conductive material disposed on a substrate. FIG. 17 is a cross-sectional view showing a process of forming an electrode structure by patterning a conductive material disposed on a substrate.

Next, the patterning step is performed. Referring to FIGS. 16 and 17, the patterning step is a step of forming an electrode structure 1500 by patterning the conductive material 1520 disposed on a substrate. In one embodiment, the conductive material 1520 may be patterned using a laser. However, it is not limited to the laser patterning.

When the patterning step is completed, the conductive material 1520 may have the shape of the electrode structure 1500 as shown in FIG. 16.

Figure 18A:
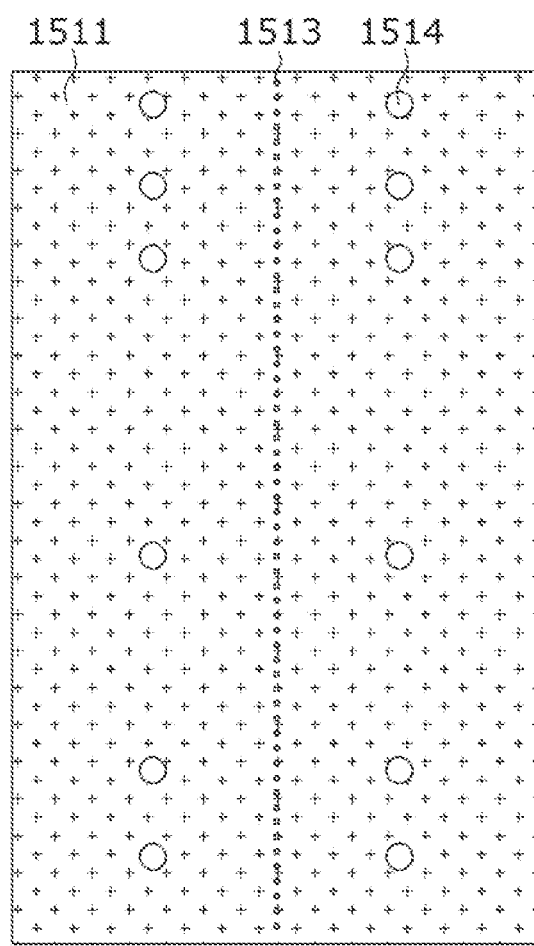
FIG. 18a is a rear view of a substrate in which folding guide grooves and alignment holes are formed on a rear surface thereof.
Figure 18B:
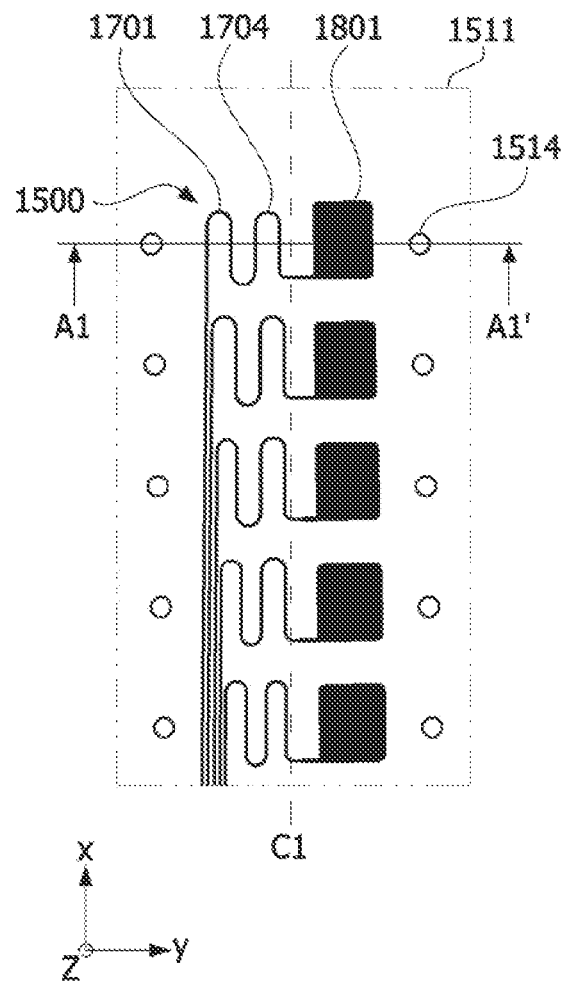
Figure 19:
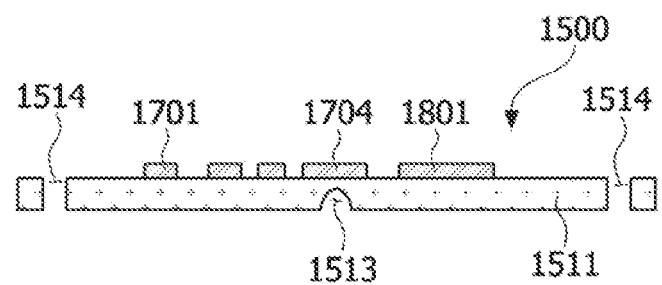
FIG. 19 is a cross-sectional view of FIG. 18b.

FIG. 18a is a rear view of a substrate in which folding guide grooves and alignment holes are formed on a rear surface thereof. FIG. 18b is a front view of FIG. 18a. FIG. 19 is a cross-sectional view of FIG. 18b.

Next, a substrate processing step may be performed. Referring to FIGS. 18a, 18b and 19, the substrate processing step is the step of forming a folding guide groove 1513 and an alignment hole 1514 by processing the rear surface of the substrate 1511. The rear surface of the substrate 1511 is a surface facing the opposite direction to the surface on which the electrode structure 1500 is formed.

The folding guide groove 1513 is a groove formed on the rear surface of the substrate 1511 to facilitate folding when the electrode structure 1500 is folded along a line to be folded. The spacing of the grooves may be appropriately modified and applied according to the body-implantable device 1 to be manufactured.

The alignment hole 1514 is a configuration that guides the electrode structure 1500 to be accurately folded when the electrode structure 1500 is folded. By checking whether the alignment holes 1514 facing each other correctly face each other when folded, the folding can be performed accurately.

The alignment hole 1514 may be formed outside a region where the electrode structure 1500 is formed on the substrate 1511. Since the alignment hole 1514 is formed to completely penetrate the substrate 1511 unlike the folding guide groove 1513, the electrode structure 1500 may be damaged if when the alignment hole is formed in a region where the electrode structure 1500 is positioned. The specific number or position of the alignment holes 1514 may be appropriately modified and applied according to the purpose and size of the body-implantable device 1 to be manufactured.

Figure 20:
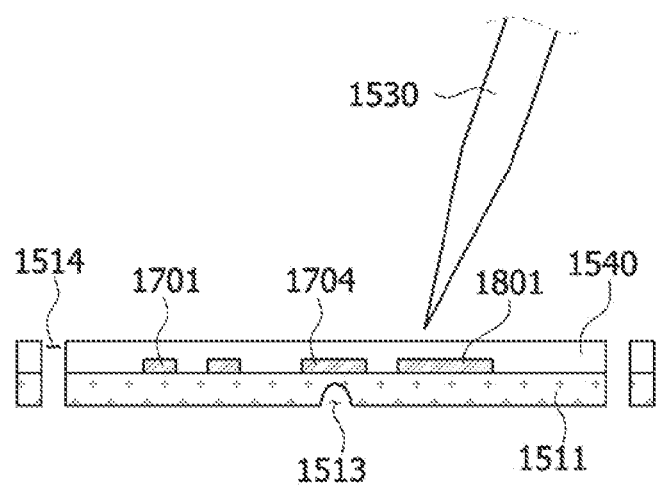
FIG. 20 is a cross-sectional view showing a process of applying an insulation material on a substrate and an electrode structure.

FIG. 20 is a cross-sectional view showing a process of applying an insulation material on a substrate and an electrode structure.

After the substrate processing step, an insulation material application step may be performed.

Referring to FIG. 20, the insulation material application step is the step for applying the insulation material 1540 on the substrate 1511 and the electrode structure 1500 formed on the substrate 1511. The insulation material 1540 may be applied using an insulation material applying device 1530.

The insulation material 1540 may include a silicone elastomer. The applied insulation material 1540 can prevent a short between the contact electrode 1801 and the contact electrode 1801, between the pad 1802 and the pad 1802, or between the contact electrode 1801, the pad 1802, and the wires 1701, 1702, 1703 and 1704, and block an unnecessary electrical signal from being introduced from an outside. In addition, the insulation material 1540 may not only insulate between components, but also strongly bond each component and fix the components at a desired position.

Figure 21:
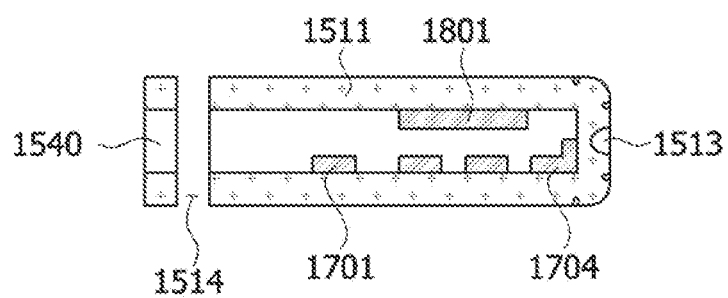
FIG. 21 is a cross-sectional view showing that a substrate and a electrode structure are folded.

FIG. 21 is a cross-sectional view showing that a substrate and an electrode structure are folded.

After the insulation material 1540 is applied, a folding step may be performed. Referring to FIG. 21, the folding step is the step for folding the substrate 1511 and the electrode structure 1500 by using the alignment hole 1514 and the folding guide groove 1513, after the insulation material 1540 is applied on the substrate 1511 and the electrode structure 1500.

The alignment hole 1514 may be configured to check whether folding is correctly performed, and the folding guide groove 1513 may be configured to facilitate folding of the substrate 1511. Such folding may be formed along the virtual line L1 in which the folding guide groove 1513 is formed. A direction in which the substrate 1511 and the electrode structure 1500 are folded may be folded in a direction in which the substrate 1511 is exposed to an outside. In other words, the substrate 1511 and the electrode structure 1500 may be folded in a direction in which the applied insulation material 1540 contacts each other. Accordingly, portions of the electrode structure 1500 may face each other and then insulation material 1540 may be positioned therebetween. The insulation material 1540 positioned between the folded and facing electrode structure 1500 may serve as an insulation layer. That is, the insulation layer may serve to prevent an unnecessary short between the contact electrode 1801 and the plurality of wires.

Additionally, in order to improve insulation performance and bonding strength, the insulation material 1540 may be reapplied one or more times just before the folding step.

Figure 22:
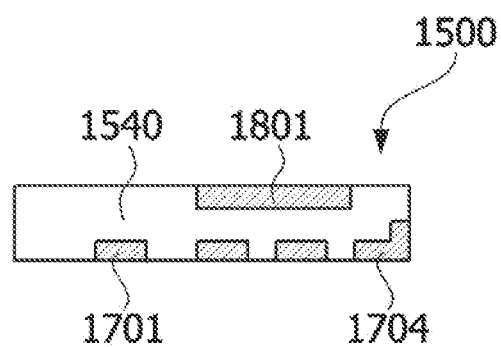
FIG. 22 is a cross-sectional view showing an electrode structure from which a substrate is removed.

FIG. 22 is a cross-sectional view showing an electrode structure from which a substrate is removed.

After the folding step, a substrate removal step may be performed. Referring to FIG. 22, the substrate removal step is a step of removing the substrate 1511 from the folded electrode structure 1500 and the insulation layer positioned between the folded electrode structure 1500. When the substrate 1511 is removed, a portion of the electrode structure 1500 may be exposed to the outside. A portion of the exposed electrode structure 1500 may be the contact electrode 1801.

Figure 23:
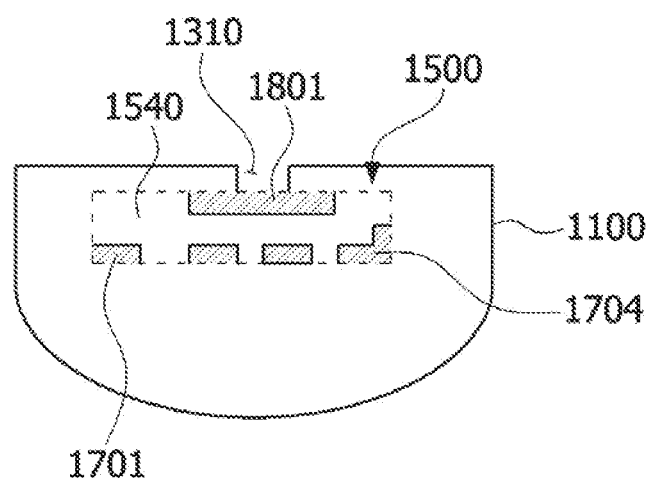
FIG. 23 is a cross-sectional view showing that a housing is formed in an electrode structure from which a substrate is removed.

FIG. 23 is a cross-sectional view showing that a housing is formed in an electrode structure from which a substrate is removed.

Next, a housing forming step may be performed. Referring to FIG. 23, after the substrate 1511 is removed, the housings 1100 and 1200 surrounding the folded electrode structure 1500 may be formed. The housings 1100 and 1200 may include the first housing 1100 and the second housing 1200 as described above, and each of the housings 1100 and 1200 may include the cover layers 1301 and 1302. The cover layers 1301 and 1302 may serve to cover the electrode structure 1500 folded as a part of the housings 1100 and 1200.

The electrode hole 1310 may be formed on a portion of the first cover layer 1301. The electrode hole 1310 is an opening exposing the contact electrode 1801 below the first cover layer 1301 to an outside. The electrode hole 1310 may be formed for each of the plurality of contact electrodes 1801. That is, one electrode hole 1310 may expose one contact electrode 1801. In this case, the number of electrode holes 1310 may be the same as the number of contact electrodes 1801. The number of electrode holes 1310 may be the same as the number of channels of the circuit 230.

The housings 1100 and 1200 and the cover layers 1301 and 1302 may all include the same material. In one embodiment, the housings 1100 and 1200 and the cover layers 1301 and 1302 may include the insulation material 1540 applied in the insulation material application step. More specifically, the housings 1100 and 1200 and the cover layers 1301 and 1302 may include a silicone elastomer. The housings 1100 and 1200 and the cover layers 1301 and 1302 formed of the same insulation material 1540, and the insulation layer may form an integral body.

Figure 24:
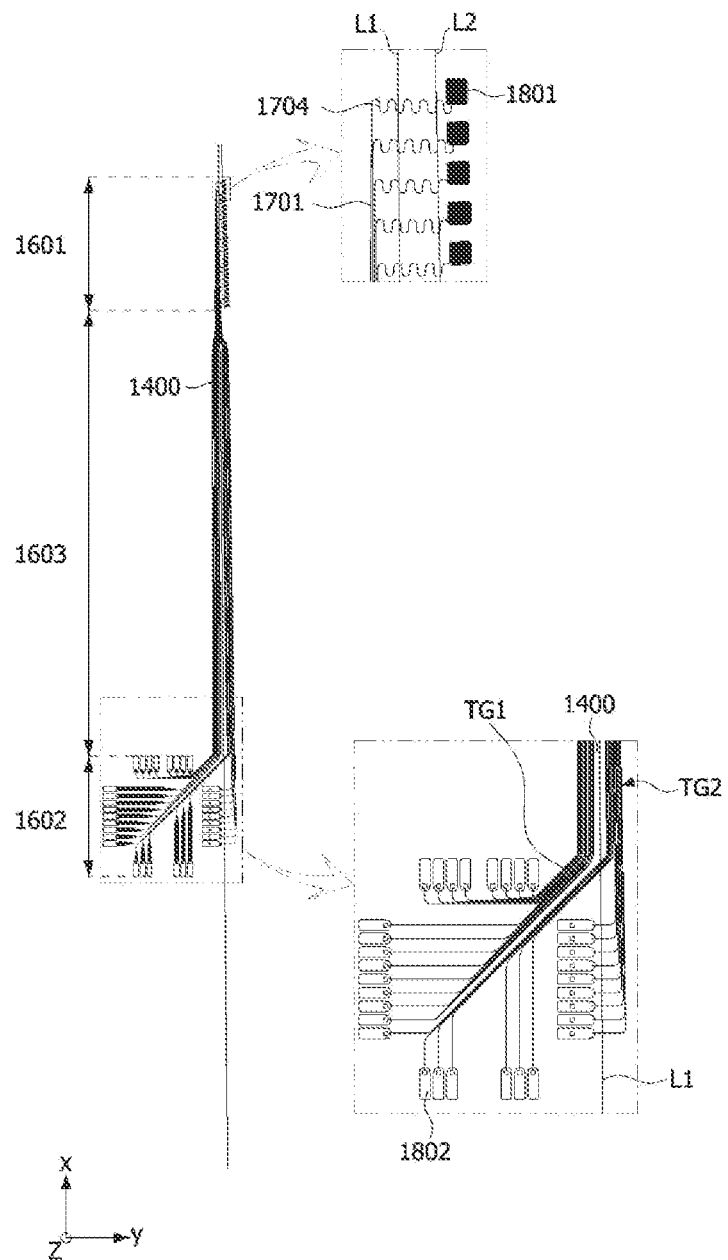
FIG. 24 is a view showing an electrode structure according to a second embodiment.

FIG. 24 is a view showing an electrode structure according to another embodiment. With respect to the electrode structure according to another embodiment of the present invention, the description of the configuration substantially the same as that described above will be simplified, and the difference will be mainly described.

Referring to FIG. 24, the electrode structure 1500 may include a contact electrode part 1601, a pad part 1602, and a connection part 1603.

The contact electrode part 1601 may be a region in which the plurality of contact electrodes 1801, the plurality of first wires 1701, and the plurality of connection wires 1704 are disposed. The pad part 1602 may be a region in which the plurality of pads 1802 and the second wire 1702 are disposed. The connection part 1603 may be a region in which the plurality of third wires 1703 is disposed and the folding part 1400 is positioned. The first wire 1701, the second wire 1702, and the third wire 1703 may be a single wire connecting the contact electrode 1801 and the pad 1802.

The electrode structure 1500 may include the virtual line L1 crossing the electrode structure 1500 in the first direction. The virtual line L1 may divide the electrode structure 1500 into two regions adjacent in the second direction. The virtual line L1 may cross the folding part 1400.

As described above, the electrode structure 1500 may be folded using the virtual line L1 as a reference line so as to form the electrode array 1000. Referring to an enlarged view of the pad part 1602 in FIG. 24, the virtual line L1 may cross the pad part 1602. When folded around the imaginary line L1, a portion of the pad part 1602 may be bent and overlapped with each other.

For example, the second wire group TG2 connected to the plurality of pads 1802 may be bent and disposed on the upper portion of the pads 1802. That is, the plurality of pads 1802 may be disposed on the lower portion, and the bent second wire group TG2 may be disposed on the upper portion. However, since an insulation layer is disposed between the plurality of pads 1802 and the second wire group TG2, they may be electrically insulated.

In the present embodiment, there is no problem in connecting the electrodes of the circuit 230 and the pads 1802 even when a portion of the pad part 1602 overlaps. This is because the pad 1802 and the pad 1802 do not overlap even if the portion of the pad part 1602 partially overlaps due to folding.

The electrode structure 1500 according to the present embodiment may be folded twice or more as needed when forming the electrode array 1500. When the electrode structure 1500 is folded n−1 (n is an integer greater than or equal to 2) times, the electrode structure 1500 may include a first line to n−1-th lines L1, L2, which are imaginary lines dividing the region into n (n is an integer greater than or equal to 2) regions along the second direction. The first line to the n−1-th lines do not cross each other and may be virtual lines extending in the first direction, respectively.

In the folding process, the electrode structure 1500 may be folded alternately by in-folding and out-folding based on the first line to the n−1-th line.

FIG. 24 shows an electrode structure 1500 that requires folding twice, that is, when n is 3. Referring to FIG. 24, the electrode structure 1500 may first be in-folded around the first line L1. Then, the electrode structure 1500 may be out-folded along the second line L2 as a center. The reason for alternately performing in-folding and out-folding is to expose the contact electrode 1801 at the outside of the completed electrode array 1000. Although it has been described that the electrode structure 1500 is folded twice in FIG. 24 as an example, the embodiment is not limited thereto.

Figure 25A:
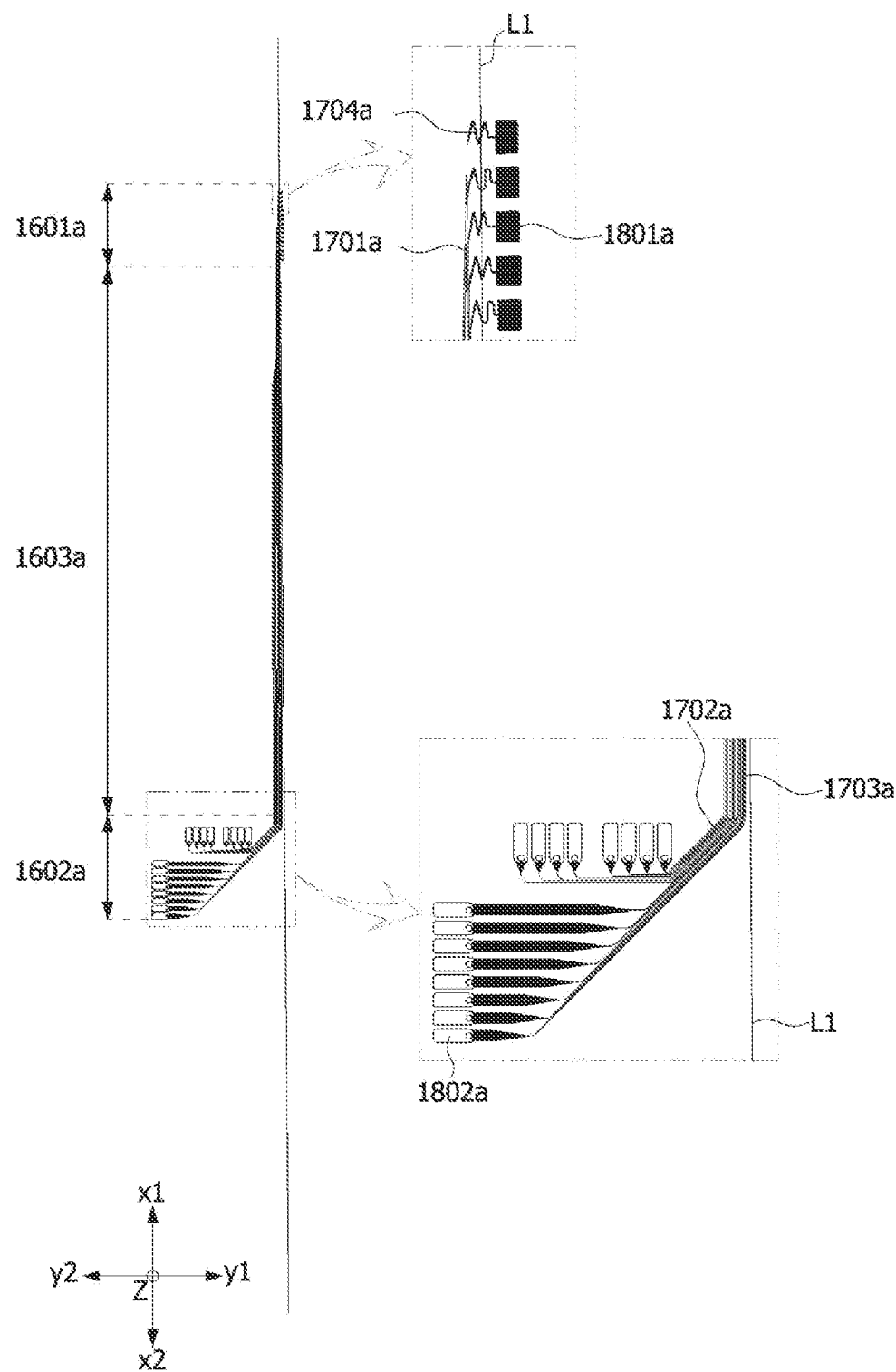
FIGS. 25a and 25b are views showing an electrode structure according to a third embodiment.
Figure 25B:
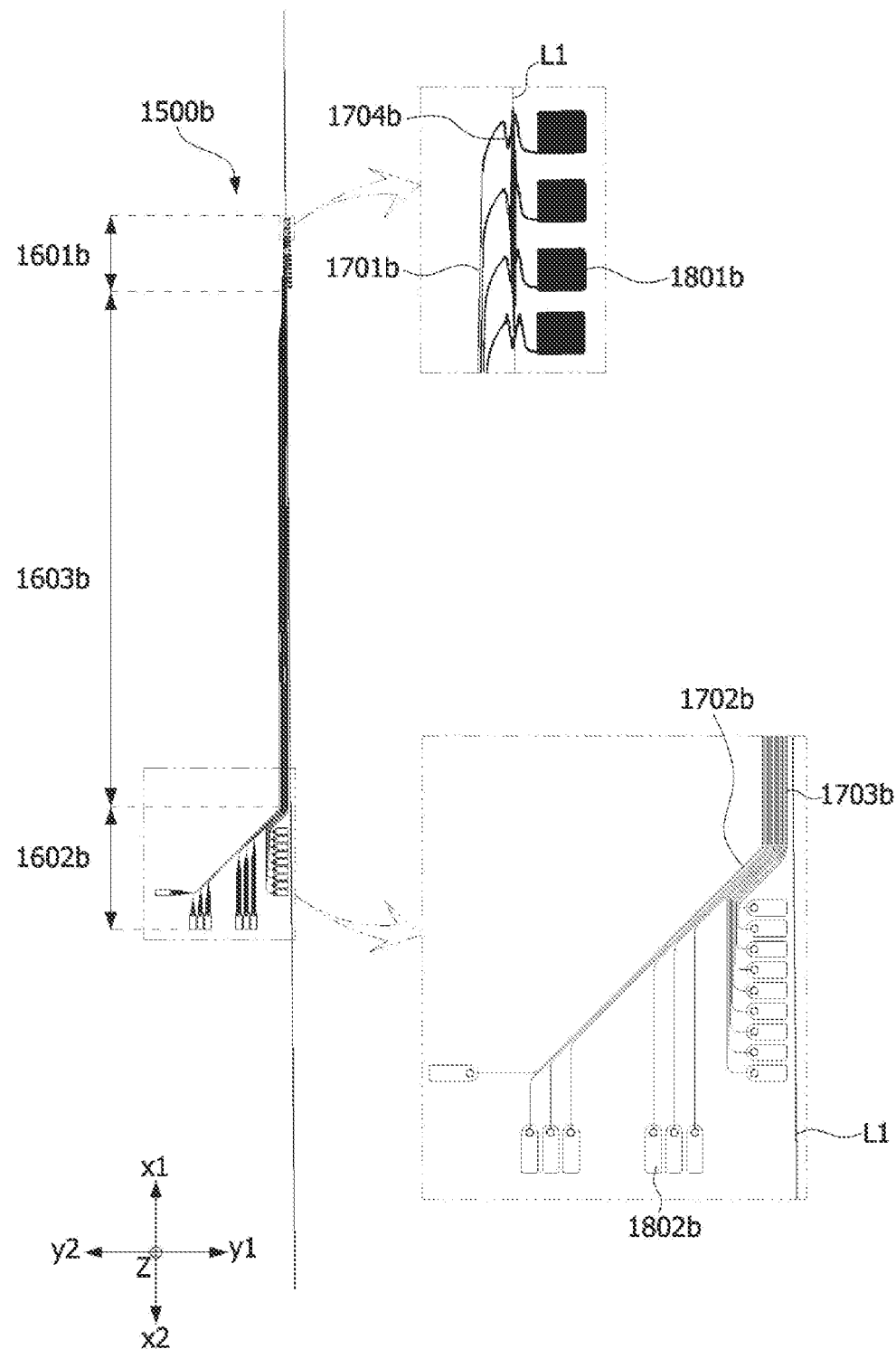

FIGS. 25a and 25b are views showing an electrode structure according to another embodiment.

The electrode structure according to the present embodiment may include a plurality of electrode structures separated from each other. Hereinafter, a set of a plurality of electrode structures will be referred to as an electrode structure group.

The electrode structure group may include a first electrode structure to an n-th (n is an integer of 2 or more) electrode structure. The first electrode structure to the n-th electrode structure may be electrode structures separated from each other.

The i-th (i is an integer greater than or equal to 1 and less than or equal to n) electrode structure may include an i-th contact electrode part, an i-th pad part, and an i-th connection part. The i-th contact electrode part, the i-th pad part, and the i-th connection part correspond to the contact electrode part 1601, the pad part 1602, and the connection part 1603 in the embodiment of FIG. 10, respectively.

The i-th contact electrode part may include a plurality of i-th connection wires extending from the plurality of i-th contact electrodes, a plurality of first-i-th wires, and a plurality of i-th connection wire to connect the plurality of i-th contact electrodes and the plurality of first-i-th wires. The i-th contact electrode, the first-i-th wire, and the i-th connection wire correspond to the contact electrode 1801, the first wire 1701, and the connection wire 1704 in the embodiment of FIG. 11, respectively.

The i-th pad part may include a plurality of i-th pads and a plurality of second-i-th wires connected to the plurality of i-th pads. The i-th pad and the second i-th wire correspond to the pad 1802 and the second wire 1702 of the embodiment of FIG. 13, respectively.

The i-th connection part may include a plurality of third-i-th wires connecting the plurality of first-i-th wires and the plurality of second-i-th wires. The third-i-th wire corresponds to the third wire 1703 of the embodiment of FIG. 12. The i-th connection part may be disposed between the i-th contact electrode part and the i-th pad part.

A length of the i-th electrode structure in the first direction may be inversely proportional to i. That is, the distance between the i-th contact electrode among the plurality of i-th contact electrodes closest to the i-th pad part and the i-th pad part may be greater than the distance between the i+1-th contact electrode among the plurality of i+1-th contact electrodes farthest from the i+1-th pad part and the i+1-th pad. This is to prevent overlapping between the first to n-th contact electrodes while overlapping a plurality of electrode structures when forming the electrode array 1000.

FIGS. 25a and 25b show forming an electrode structure group having two electrode structures, that is, when n is 2. For convenience of description, a case in which n is 2 will be described as an example, but n is not limited to 2.

When n is 2, the electrode structure group may include a first electrode structure 1500a and a second electrode structure 1500b.

FIG. 25a is a view showing a first electrode structure.

Referring to FIG. 25a, the first electrode structure 1500a may include a first contact electrode part 1601a, a first pad part 1602a, and a first connection part 1603a.

The first contact electrode part 1601a may include a plurality of first contact electrodes 1801a, a plurality of first-1 wires 1701a, and a plurality of first connection wire 1704a extending from the plurality of first contact electrodes 1801a to connect the plurality of first contact electrodes 1801a and the plurality of first-1 wires 1701a. The first pad part 1602a may include a plurality of first pads 1802a and a plurality of second-1 wires 1702a connected to the plurality of first pads 1802a.

The first connection part 1603a may include a plurality of third-1 wires 1703a connecting the plurality of first-1 wires 1701a and the plurality of second-1 wires 1702a. The first connection part 1603a may be disposed between the first contact electrode part 1601a and the first pad part 1602a.

The first electrode structure 1500a may undergo the same process as in the above-described embodiments until the substrate removal step shown in FIG. 22 to form the electrode array 1000.

The first electrode structure 1500a may include the first line L1 that is the virtual line crossing the plurality of first connection wires 1704a in the first direction. In the process of forming the electrode array 1000, the first electrode structure 1500a may be folded based on the first line L1. More specifically, the first contact electrode part 1601a of the first electrode structure 1500a may be folded based on the first line L1. When the first contact electrode part 1601a is folded based on the first line L1, the plurality of first contact electrodes 1801a and the plurality of first-1 wires 1701a may be overlapped in the third direction with the insulation film interposed therebetween. The first contact electrode part 1601a and the first connection part 1603a may be disposed in the first groove of the first housing, and the first pad part 1602a may be disposed in the second groove of the second housing.

Referring to FIG. 25b, the second electrode structure 1500b may include a second contact electrode part 1601b, a second pad part 1602b, and a second connection part 1603b.

The second contact electrode part 1601b may include a plurality of second contact electrodes 1801b, a plurality of first-2 wires 1701b, and a plurality of second connection wires 1704b extending from the plurality of second contact electrodes 1801b to connect the plurality of second contact electrodes 1801b and the plurality of first-2 wires 1701b.

The second pad part 1602b may include a plurality of second pads 1802b and a plurality of second-2 wires 1702b connected to the plurality of second pads 1802b.

The second connection part 1603b may include a plurality of third-2 wires 1703b connecting the plurality of first-2 wires 1701b and the plurality of second-2 wires 1702b. The second connection part 1603b may be disposed between the second contact electrode part 1601b and the second pad part 1602b.

Similarly, the second electrode structure 1500b may undergo the same process as in the above-described embodiments until the substrate removal step shown in FIG. 22 to form the electrode array 1000.

The second electrode structure 1500b may include the first line L1 that is the virtual line crossing the plurality of second connection wires 1704b in the first direction. In the process of forming the electrode array 1000, the second electrode structure 1500b may be folded based on the first line L1. More specifically, the second contact electrode part 1601b of the second electrode structure 1500b may be folded based on the first line L1. When the second contact electrode part 1601b is folded based on the first line L1, the plurality of second contact electrodes 1801b and the plurality of first-2 wires 1701b may be overlapped in the third direction with the insulation layer interposed therebetween. The second contact electrode part 1601b and the second connection part 1603b may be disposed in the first groove of the first housing, and the second pad part 1602a may be disposed in the second groove of the second housing.

In the present embodiment, a process of stacking the first electrode structure 1500a and the second electrode structure 1500b is further performed to form the electrode array 1000.

Figure 26:
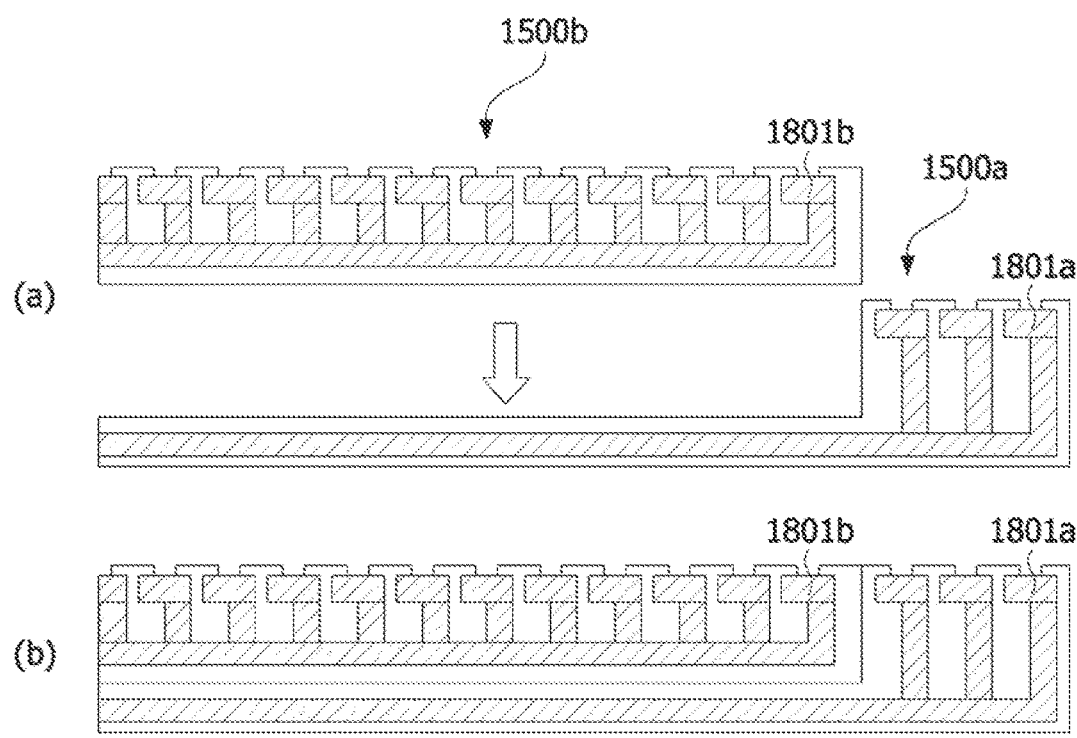
FIG. 26 is a view showing a process of laminating a first electrode structure and a second electrode structure.

FIG. 26 is a view showing a process of stacking the first electrode structure 1500a and the second electrode structure 1500b.

Referring to (a) of FIG. 26, the second electrode structure 1500b may be disposed on the first electrode structure 1500a. In order to minimize the step difference between the first contact electrode 1801a and the second contact electrode 1801b after the electrode structures 1500a and 1500b are stacked, some of the insulation material 1540 covering the first electrode structure 1500a may be removed. The insulation material 1540 may serve as an insulation layer between the respective components. When the second electrode structure 1500a is disposed at the place where the insulation material 1540 is removed, the step difference between the first contact electrode 1801a and the second contact electrode 1801b may be minimized as shown in (b) of FIG. 26.

Hereinafter, the lengths of the first electrode structure 1500a and the second electrode structure 1500b in the first direction will be described with reference to FIGS. 25a, 25b, and 26.

The plurality of first contact electrodes 1801a may include a first-1 contact electrode to a first-s (s is an integer greater than or equal to 1) contact electrode that are sequentially arranged in the first direction from a point far from the first pad part 1602a. That is, the first-1 contact electrode may be a contact electrode furthest from the first pad part 1602a, and the first-s-th contact electrode may be a contact electrode closest to the first pad part 1602a.

The plurality of second contact electrodes 1801b may include a second-1 contact electrode to a second-t-th contact electrode (t is an integer greater than or equal to 1) that are sequentially arranged in the first direction from a point far from the second pad part 1602b. That is, the second-1 contact electrode may be a contact electrode furthest from the second pad part 1602b, and the second-t-th contact electrode may be a contact electrode closest to the second pad part 1602b.

A distance between the first-s-th contact electrode and the first pad part 1602a may be greater than a distance between the second-1 contact electrode and the second pad part 1602b. That is, the distance between the first-s-th contact electrode positioned closest to the first pad part 1602a and the first pad part 1602a may be greater than the distance between the first-s-th contact electrode positioned farthest from the second pad part 1602b and the second pad part 1602b. Otherwise, that is, if the distance between the second-1 contact electrode and the second pad part 1602b is greater than the distance between the first-s-th contact electrode and the first pad part, some of the plurality of the second contact electrode 1801b may overlap some of the plurality of first contact electrodes 1801a.

The length of the first electrode structure 1500a in the first direction may be greater than the length of the second electrode structure 1500b in the first direction. It is because the plurality of second contact electrodes 1801b may overlap the plurality of first contact electrodes 1801a if the length of the first electrode structure 1500a in the first direction is smaller than the length of the second electrode structure 1500b in the first direction.

The plurality of first-2 wires 1701b and the plurality of second contact electrodes 1801b may be stacked with the third-1 wire 1703c with an insulation layer interposed therebetween. Also, the plurality of third-1 wires 1703a and the plurality of third-2 wires 1703b may overlap in the third direction with an insulation layer interposed therebetween.

Referring to FIGS. 25a and 25b, the first connection wire 1704a and the second connection wire 1704b may include a moire pattern or a zigzag pattern.

Referring to FIGS. 25a and 25b, the first pad part 1602a and the second pad part 1602b may have a pattern so that the first pad part 1602a and the second pad part 1602b do not overlap each other when the second electrode structure 1500b is stacked on the first electrode structure 1500a. For example, as shown in FIG. 25a, the first pad part 1602a may be patterned such that the first pad 1802a and the second-1 wire 1702a face the X1 direction and the Y2 direction, As shown in FIG. 25b, the second pad part 1602b may be patterned such that the second pad 1802b and the second-2 wire 1702b face the X2 direction and the Y1 direction.

Figure 27:
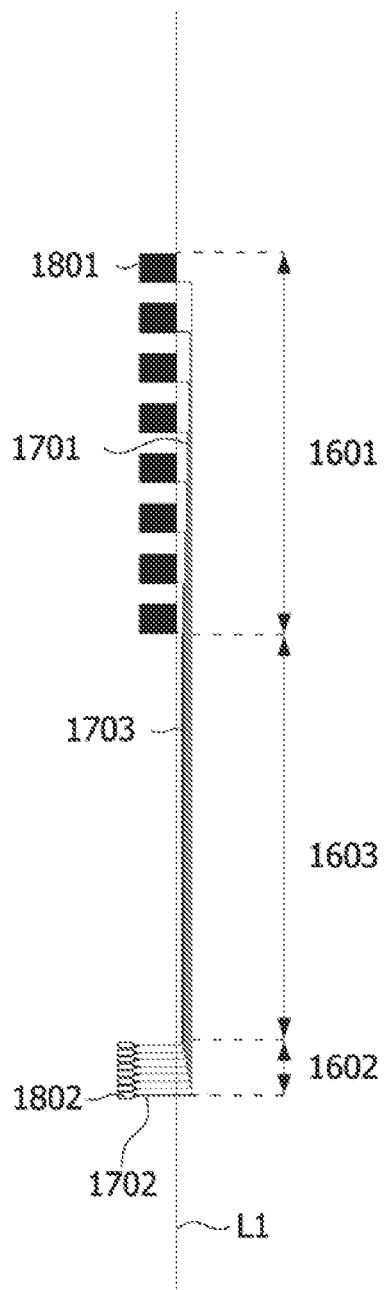
FIG. 27 is a view showing an electrode structure according to a fourth embodiment.

FIG. 27 is a view showing an electrode structure according to another embodiment.

Referring to FIG. 27, the electrode structure 1500 may include the contact electrode part 1601, the pad part 1602, and the connection part 1603.

The contact electrode part 1601 may be a region in which the plurality of contact electrodes 1801, the plurality of first wires 1701, and the plurality of connection wires 1704 are disposed. The pad part 1602 may be a region in which the plurality of pads 1802 and the second wire 1702 are disposed. The connection part 1603 may be a region in which the plurality of third wires 1703 is disposed.

The electrode structure 1500 may include the virtual line L1 that crosses the electrode structure 1500 in the first direction. The virtual line L1 may divide the electrode structure 1500 into two regions adjacent in the second direction.

Figure 28:
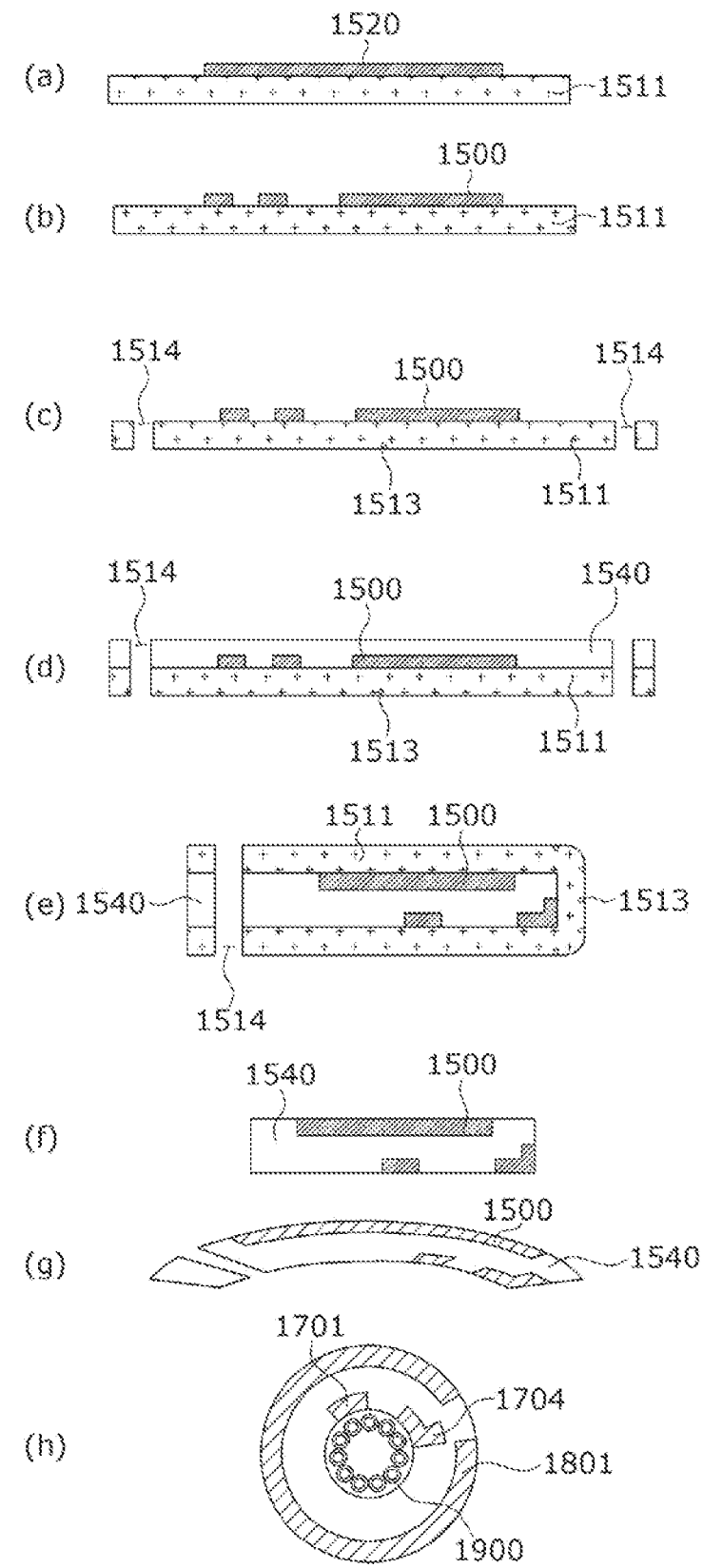
FIG. 28 is a view showing a process of manufacturing an electrode array according to a fourth embodiment.

FIG. 28 is a view showing a process of manufacturing an electrode array according to an embodiment.

The manufacturing process in (a) to (f) of FIG. 28 may be substantially the same as the manufacturing process described with reference to FIGS. 14 to 22.

Step (a) is a step of forming the conductive material 1520 on the substrate 1511. Step (b) shows the step of forming the electrode structure 1500 by patterning the conductive material 1520 into a desired shape. Step (c) is a step of forming the alignment hole 1514 and the folding guide groove 1513 by processing the substrate 1511. Step (d) shows a process of covering the patterned electrode structure 1500 by applying the insulation material 1540 on the substrate 1511. Step (e) shows a process of folding the substrate 1511, the insulation material 1540, and the electrode structure 1500. The folding may be formed based on the virtual line L1 of FIG. 27. Step (f) shows a process of removing the substrate 1511 from the folded electrode structure 1500. In this process, the contact electrode 1801 may be exposed to an outside.

Steps (g) and (h) are steps of forming the folded electrode structure 1500 in a cylindrical shape. More specifically, the electrode structure 1500 may be manufactured in a cylindrical shape in which the contact electrode 1801 exposed to the outside by step (f) is positioned on the outer circumferential surface. A core bundle 1900 may be disposed on the inner circumferential surface (or inside) of the cylindrical shape. The core bundle 1900 may serve as a skeleton for maintaining the shape of the completed electrode array 1000. At the same time, the core bundle 1900 may serve to guide a stylette, as will be described later, in the body implantation stage of the electrode array 1000.

The core bundle 1900 may have flexibility. This is to suppress excessive pressure on surrounding tissues after implantation into the body. To this end, the core bundle 1900 may include a coil spring having stainless steel.

The core bundle 1900 may serve to assist the electrode array 1000 to be implanted at an accurate site in the body. More specifically, the core bundle 1900 may form a hole penetrating the center of the electrode array 1000, and may be implanted at an accurate site using the stylette disposed in the hole. The stylette is an auxiliary tool having straightness and rigidity above a certain level, and may serve to assist the electrode array 1000 having flexibility to reach an accurate position. The stylette is used only in the implantation stage, and may be removed from the electrode array 1000 after implantation. This is to prevent the stylette with straightness from causing damage by applying pressure on the surrounding tissue.

Figure 29:
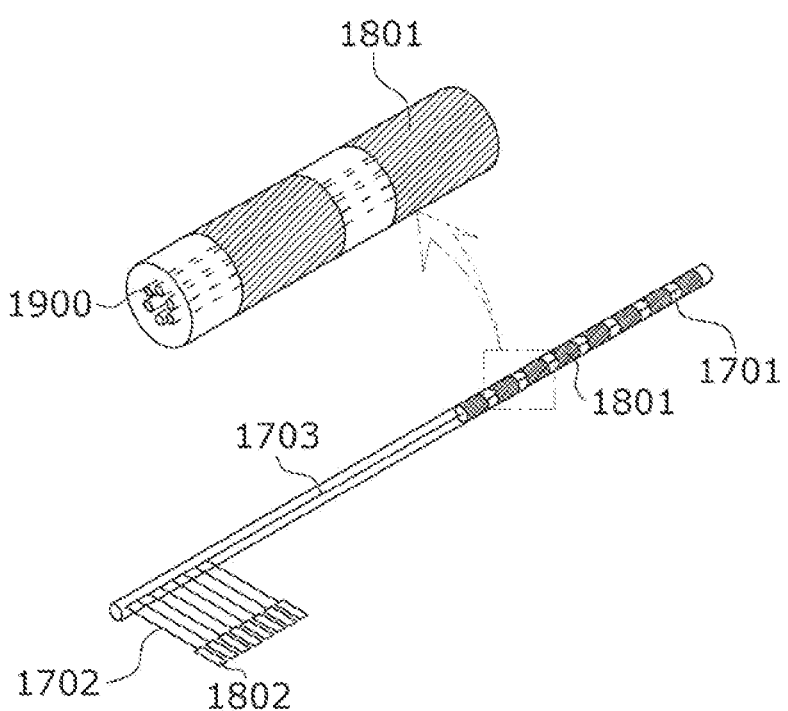
FIG. 29 is a view showing an electrode array according to a fourth embodiment.

FIG. 29 is a view showing an electrode array according to an embodiment.

Referring to (h) of FIG. 28 and FIG. 29, the core bundle 1900 serving as a skeleton may be positioned on the inner circumferential surface (or inside) of the electrode array 1000. The wires 1701, 1702, 1703, and 1704 may be positioned outside the core bundle 1900. An insulation layer may be positioned outside the core bundle 1900 and the wires 1701, 1702, 1703, and 1704. The plurality of contact electrodes 1801 exposed to the outside may be positioned outside the insulation layer.

A plurality of contact electrodes may be positioned at one end of the cylindrical electrode array 1000. The plurality of pads 1802 exposed to the outside and connected to the circuit 230 may be positioned at the other end of the cylindrical electrode array 1000.

Figure 30:
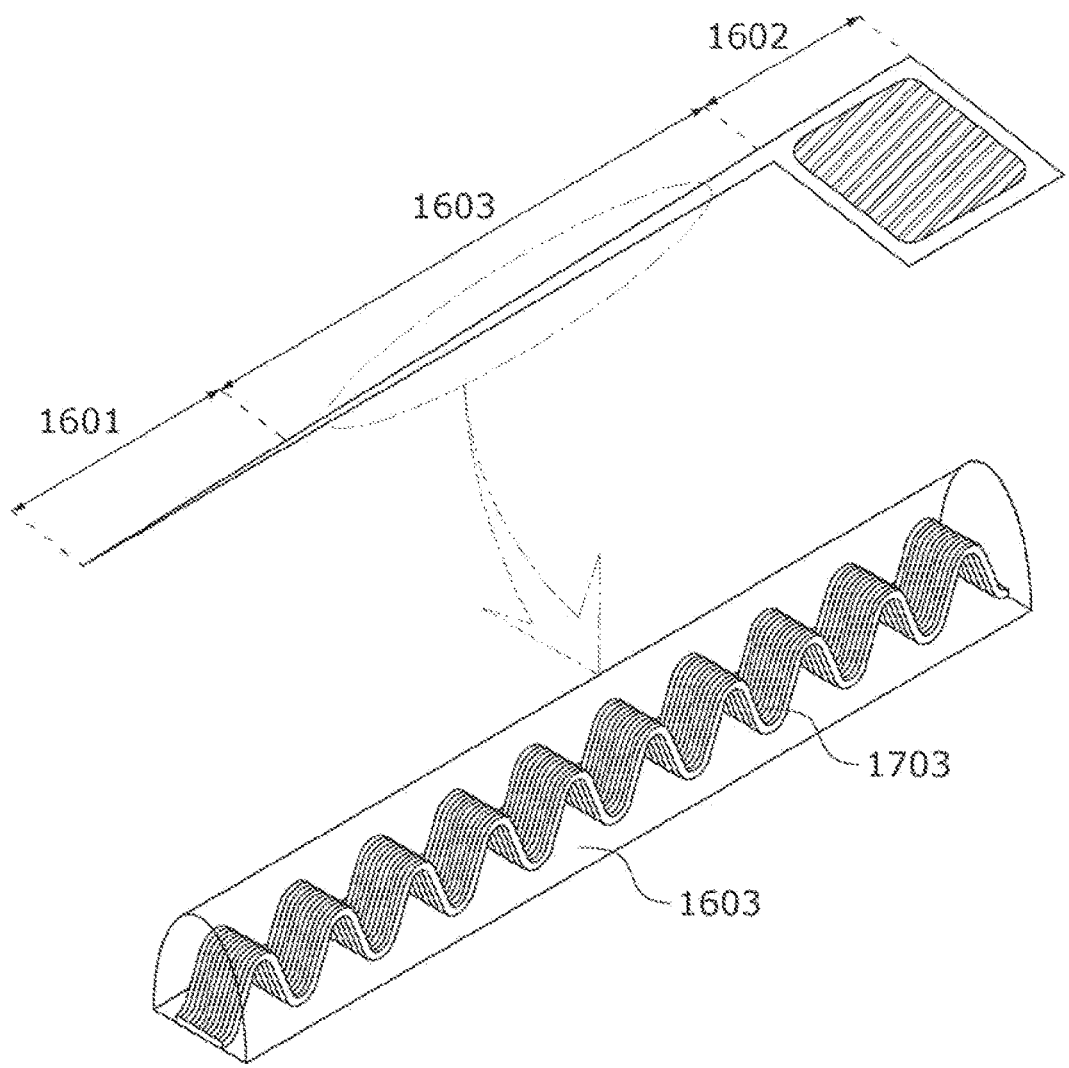
FIG. 30 is a view showing an electrode array according to a fifth embodiment.

FIG. 30 is a view showing an electrode array according to an embodiment.

Referring to FIG. 30, the electrode array 1000 may be bent in a body as necessary. For flexibility and stability, the wires may include a moire pattern or a wave pattern. In FIG. 30, the third wires 1703 have a moire pattern or a wave pattern as an example, but the embodiment is not limited thereto, and all wires of the above-described embodiments may include such a pattern to improve flexibility and stability. The patterns that the wires may have may include not only a moire pattern or a wave pattern, but also various patterns that help improve flexibility and stability.

Figure 31:
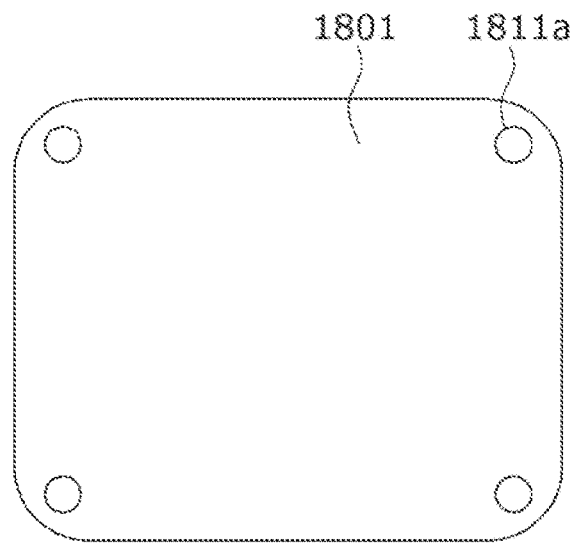
FIG. 31 is a view showing an embodiment of a contact electrode.

FIG. 31 is a view showing an embodiment of a contact electrode.

Referring to FIG. 31, the contact electrode 1801 may have a rectangular shape with curved vertices. Also, the contact electrode 1801 may include a plurality of fixing holes 1811a. In an embodiment, the fixing hole 1811a may be formed at each vertex of the contact electrode 1801. However, the shape of the contact electrode 1801 and the number and position of the fixing holes 1811a are exemplary and may be appropriately modified according to circumstances.

Figure 32:
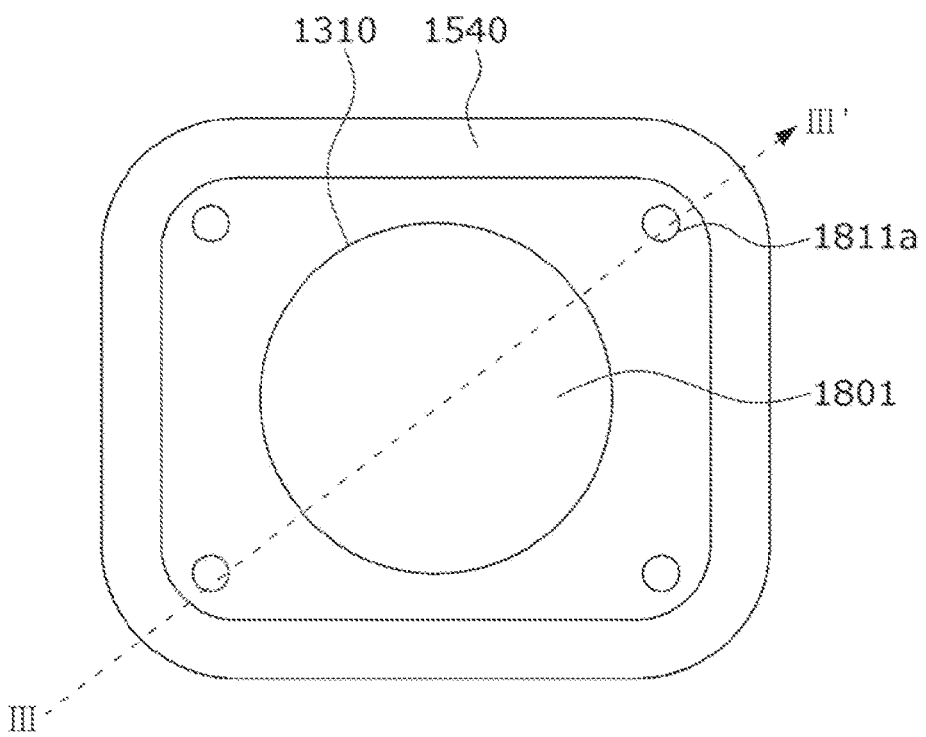
FIG. 32 is a view showing a contact electrode coated with an insulation material.
Figure 33:
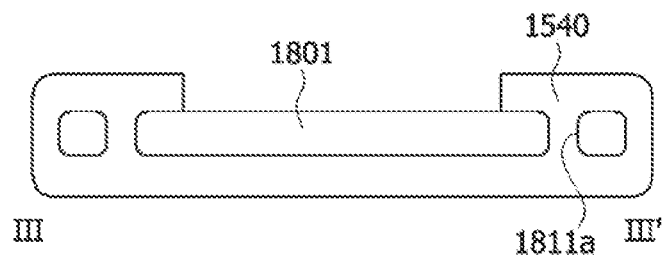
FIG. 33 is a cross-sectional view taken along line III-III' of FIG. 32.

FIG. 32 is a view showing a contact electrode coated with an insulation material. FIG. 33 is a cross-sectional view taken along line III-III' of FIG. 32.

Referring to FIGS. 32 and 33, the fixing hole 1811a is configured to more strongly fix the contact electrode 1801. More specifically, in fixing each configuration of the electrode array 1000 by applying the insulation material 1540, the fixing hole 1811a may play a role in more stably fixing by introducing the insulation material 1540 into the fixing hole 1811a formed in the contact electrode 1801.

Figure 34:
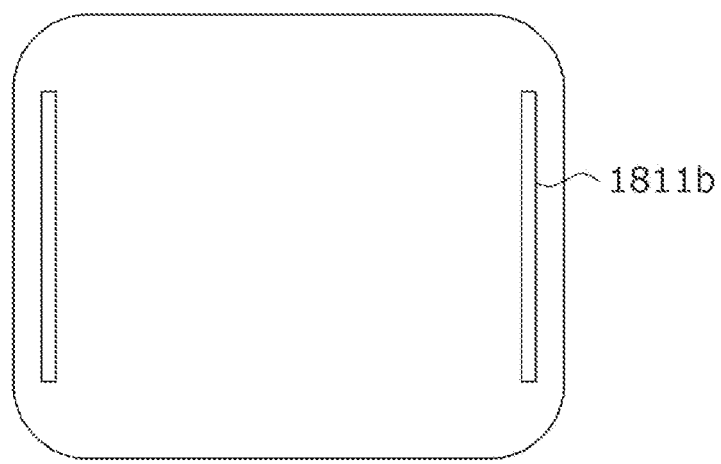
FIG. 34 is a view showing another embodiment of a contact electrode.
Figure 35:
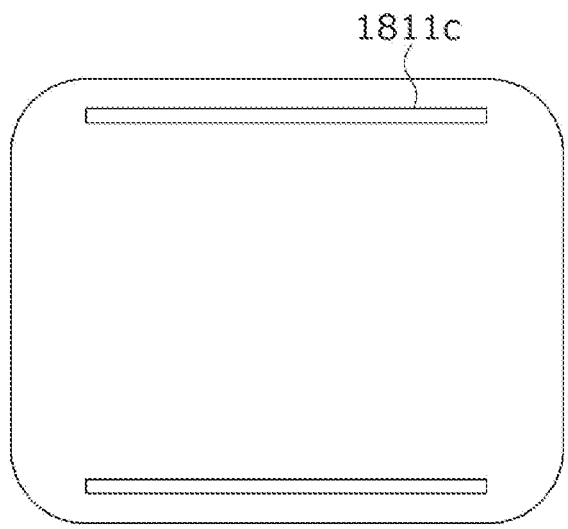
FIG. 35 is a view showing still another embodiment of a contact electrode.

FIG. 34 is a view showing another embodiment of a contact electrode. FIG. 35 is a view showing still another embodiment of a contact electrode.

Referring to FIGS. 34 and 35, the fixing holes 1811b and 1811c may be disposed on both sides of the contact electrode 1801. That is, the fixing holes may be formed in a long bar shape in the left and right or upper and lower regions of the contact electrode 1801.

Figure 36:
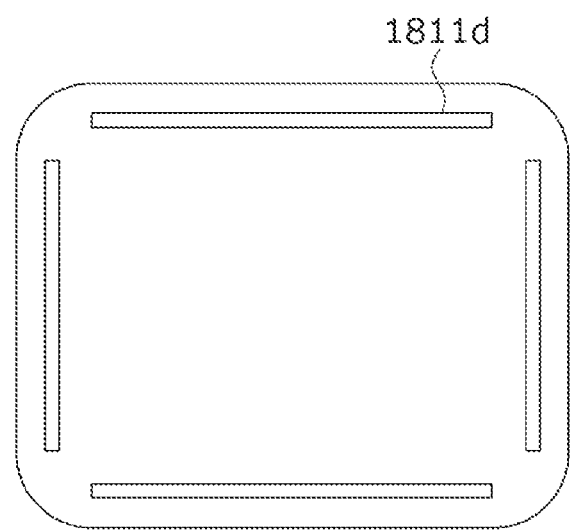
FIG. 36 is a view showing still further another embodiment of a contact electrode.

FIG. 36 is a view showing still another embodiment of a contact electrode.

Referring to FIG. 36, the fixing hole 1811d may be formed in a long bar shape in all four regions of upper, lower, left and right of the contact electrode 1801.

Conventionally, in manufacturing a body-implantable device, the electrodes in contact with a body and the wires connected to the electrodes are individually welded. In this case, there is a limit in increasing the number of electrodes per unit length.

In the electrode structure 1500 according to the above-described embodiment, the contact electrode 1801 and the wire are integrally formed, and they are folded or bended in a cylindrical shape to manufacture the electrode array 1000 and the body-implantable device 1 including the same. Therefore, manufacturing precision is increased, and thus the number of electrodes per unit length can be significantly increased. That is, the electrode structure 1500, the electrode array 1000, and the body-implantable device 1 according to the embodiment can increase the number of first electrodes 1801 that can be disposed per unit length, so that the performance and precision can be improved.

Figure 37:
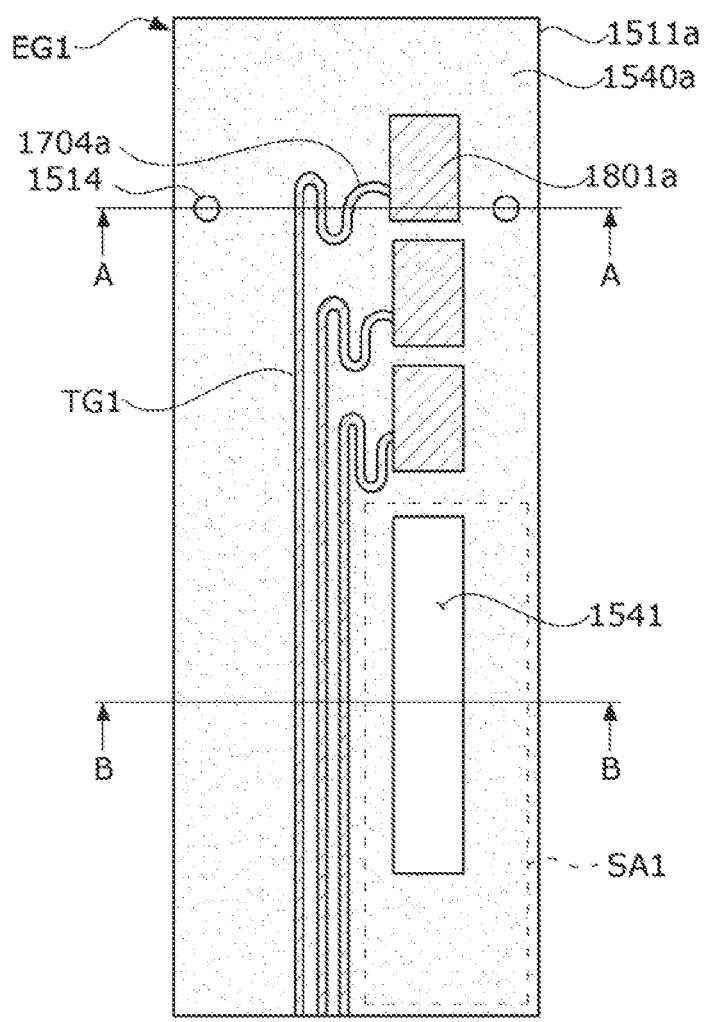
FIG. 37 is a view showing a first electrode structure of an electrode array according to a sixth embodiment.
Figure 38:
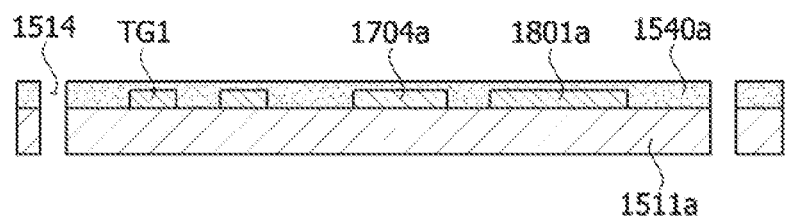
FIG. 38 is a cross-sectional view taken along A-A direction of FIG. 37.
Figure 39:
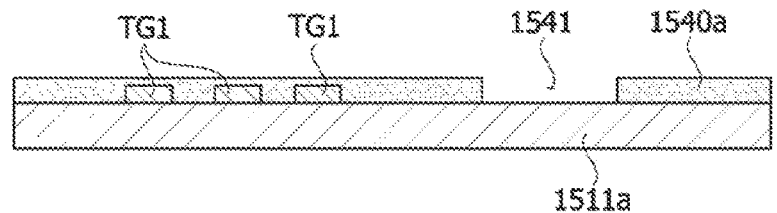
FIG. 39 is a cross-sectional view taken along B-B direction of FIG. 37.

FIG. 37 is a view showing a first electrode structure of an electrode array according to a sixth embodiment. FIG. 38 is a cross-sectional view taken along A-A direction of FIG. 37. FIG. 39 is a cross-sectional view taken along B-B direction of FIG. 37.

According to an embodiment, a first electrode structure EG1 and a second electrode structure EG2 may be respectively manufactured, and an electrode array may be manufactured by combining them.

Referring to FIGS. 37 and 38, in a first electrode structure EG1 a first electrode pattern may be formed by forming a conductive material on the first substrate 1511a and then performing a patterning. The first electrode pattern may include the first wire group TG1 and the plurality of first contact electrodes 1801a. The wire group may include the above-described first wire, second wire, and third wire.

For example, the first contact electrode 1801a of sixteen may be formed, but the number of first contact electrodes 1801a is not necessarily limited thereto.

The first connection wire 1704a may be formed between the first wire group TG1 and the first contact electrode 1801a, respectively. As described above, the first connection wire 1704a may have various curved shapes for flexibility and stability when bending. The first insulation layer 1540*a* may be formed on the first wire group TG1 and the plurality of first contact electrodes 1801*a*. Also, the alignment hole 1514 may be formed in the first substrate 1511*a*.

Referring to FIG. 39, a through hole 1541 in which the second contact electrode 1801*b* of the second electrode structure EG2 is disposed may be formed in the first insulation layer 1540*a*. The through hole 1541 may be formed to correspond to or larger than the area of the second contact electrode in order to expose the second contact electrode.

Figure 40:
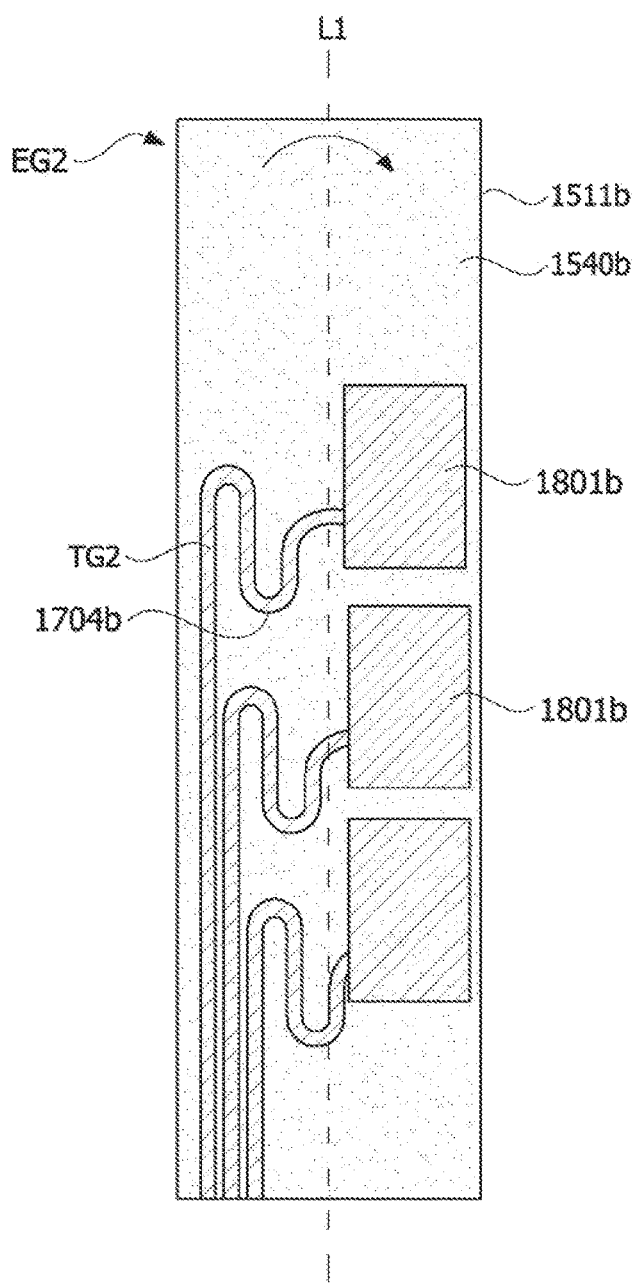
FIG. 40 is a view showing a second electrode structure of an electrode array according to a sixth embodiment.
Figure 41:
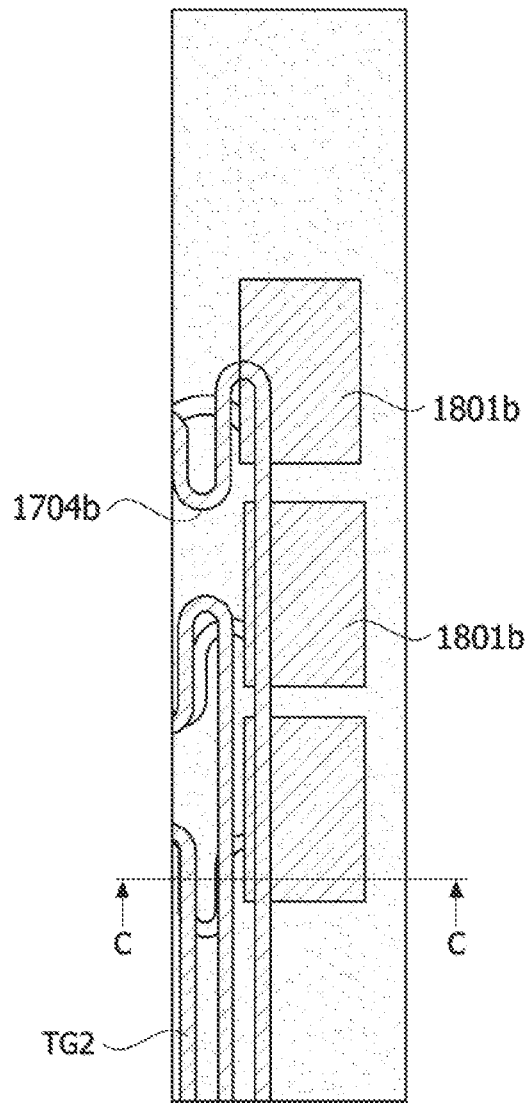
FIG. 41 is a view showing a state in which a second electrode structure is folded based on an imaginary line.
Figure 42:
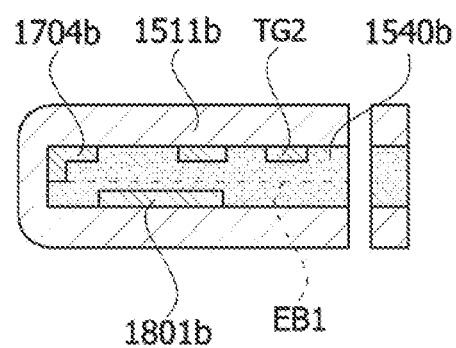
FIG. 42 is a cross-sectional view in C-C direction of FIG. 41.
Figure 43:
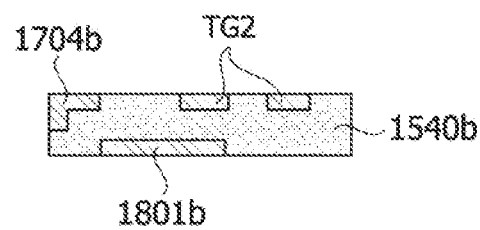
FIG. 43 is a view showing a state in which a second electrode structure is separated from a substrate.

FIG. 40 is a view showing a second electrode structure of an electrode array according to a sixth embodiment. FIG. 41 is a view showing a state in which the second electrode structure is folded based on an imaginary line. FIG. 42 is a cross-sectional view in C-C direction. FIG. 43 is a view showing a state in which the second electrode structure is separated from the substrate.

Referring to FIG. 40, in the second electrode structure EG2, a second electrode pattern may be formed by forming a conductive material on the second substrate 1511*b* and performing a patterning. The second electrode pattern may include the second wire group TG2 and the plurality of second contact electrodes 1801*b*. For example, the second contact electrode 1801*b* of sixteen may be formed, but the number is not limited thereto.

The second connection wire 1704*b* may be formed between the second wire group TG2 and the second contact electrode 1801*b*, respectively. The second insulation layer 1540*b* may be formed on the second wire group TG2 and the plurality of second contact electrodes 1801*b*. The second electrode structure EG2 may be folded along the virtual line L1 crossing the plurality of second connection wires 1704*b*.

Referring to FIGS. 41 and 42, in the process of folding the second electrode structure EG2 along the virtual line, the second connection wire 1704*b* may be disposed on a different plane from the second contact electrode 1801*b*. Here, the meaning of different plane may be defined as a horizontal plane having a different height based on a reference plane.

Since the second electrode structure EG2 is bent so that the upper surface of the second insulation layer 1540*b* faces each other, the interface EB1 of the folded second insulation layer 1540*b* may not be observed. Thereafter, as shown in FIG. 43, the second electrode structure EG2 may be manufactured by removing the second substrate 1511*b*.

Figure 44:
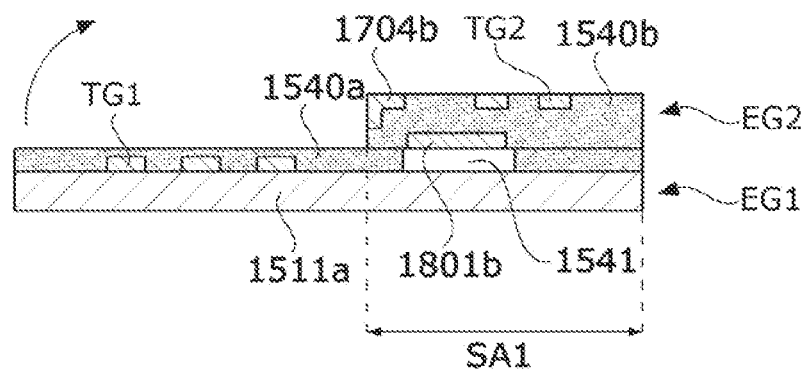
FIG. 44 is a view showing a state in which a second electrode structure is stacked on a first electrode structure.
Figure 45:
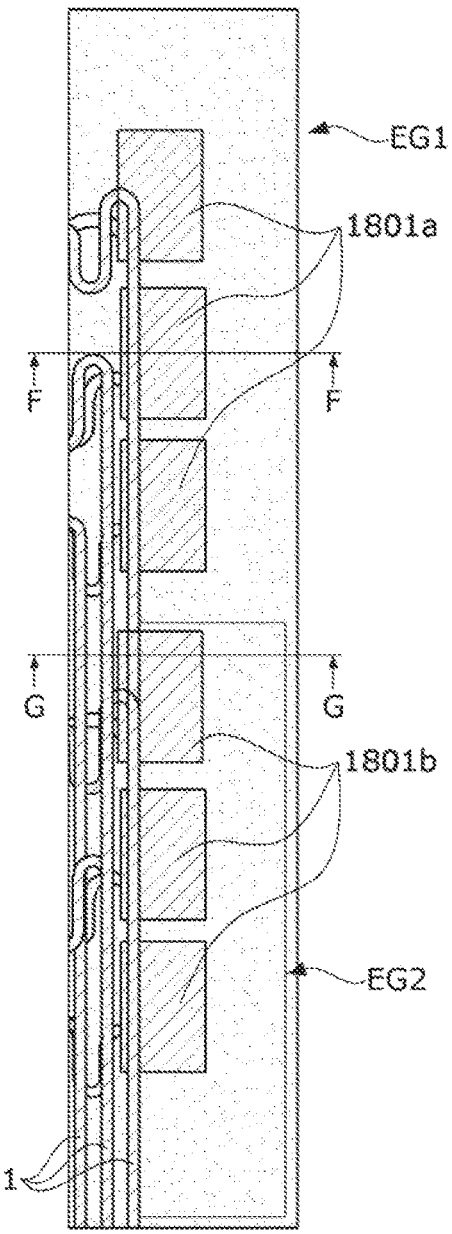
FIG. 45 is a view showing a state in which a first electrode structure is folded based on an imaginary line.
Figure 46A:
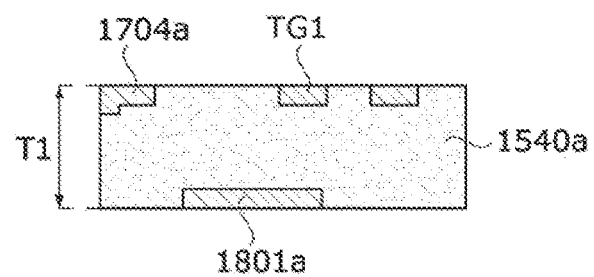
FIG. 46a is a cross-sectional view in F-F direction of FIG. 45.
Figure 46B:
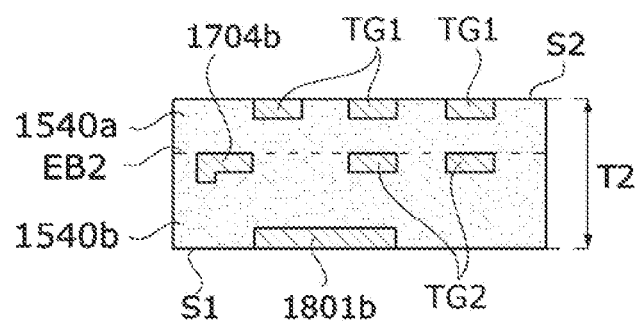
FIG. 46b is a cross-sectional view in G-G direction of FIG. 46.

FIG. 44 is a view showing a state in which a second electrode structure is stacked on a first electrode structure. FIG. 45 is a view showing a state in which the first electrode structure is folded based on an imaginary line. FIG. 46*a* is a cross-sectional view in F-F direction of FIG. 45. FIG. 46*b* is a cross-sectional view in G-G direction of FIG. 46.

Referring to FIG. 44, the second electrode structure EG2 may be stacked on a stack area SA1 of the first electrode structure EG1. The second contact electrode 1801*b* of the second electrode structure EG2 may be disposed at a position corresponding to the through hole 1541 of the first insulation layer 1540*a*. The second contact electrode 1801*b* may be exposed though the through hole 1541.

The second contact electrode 1801*b* may be inserted into the through hole 1541, but the embodiment is not limited thereto, and the second contact electrode 1801*b* may be disposed on the upper portion of the through hole 1541.

Thereafter, the first electrode structure EG1 may be folded to surround the second electrode structure EG2. After the first electrode structure EG1 is folded to surround the second electrode structure EG2, the first substrate 1511*a* may be removed.

Referring to FIG. 45, the first wire group TG1 and the second wire group TG2 may be bent in a plan view to partially overlap the first and second contact electrodes 1801*a* and 1801*b*. In this case, the width of the electrode array may be made narrower by the overlapping width. However, the embodiment is not limited thereto, and the first and second wire groups TG1 and TG2 may not overlap the first and second contact electrodes 1801*a* and 1801*b* in a plan view.

Referring to FIG. 46*a*, in a cross-section of a portion where only the first electrode structure EG1 is disposed, the first contact electrode 1801*a* is disposed on one side of the first insulation layer 1540*a*, and the first connection wire 1704*a* is bent. Thus, the first wire group TG1 may be disposed on the other side of the first insulation layer 1540*a*.

Referring to FIG. 46*b*, in a cross-section of a portion where the first electrode structure EG1 and the second electrode structure EG2 are stacked, the second contact electrode 1801*b* is disposed on one side S1 of the second insulation layer 1540*b*, and the second connection wire 1704*b* is bent, so that the second wire group TG2 may be disposed on the other side of the second insulation layer 1540*b*. A thickness T2 of a stack area may be greater than a thickness T1 of the first electrode structure EG1.

In this case, the first insulation layer 1540*a* may be stacked on the second insulation layer 1540*b* and the first wire group TG1 may be disposed on the other side S2 of the first insulation layer 1540*a*. In this case, an interface EB2 between the first insulation layer 1540*a* and the second insulation layer 1540*b* may form one insulation layer that is not observed.

According to the embodiment, the first wire group TG1 and the second wire group TG2 may be disposed on different planes. For example, the second wire group TG2 may be disposed on the interface EB2 between the insulation layers, and the first wire group TG1 may be disposed on the upper surface of the insulation layer. That is, in the thickness direction, the second wire group TG2 may be disposed in a region between the second contact electrode 1801*b* and the first wire group TG1.

According to this configuration, the wires can be disposed on different planes, so that the width and/or thickness of the electrode array may be reduced.

When manufactured in the same configuration as in the embodiment, since a smaller number of wires is disposed within the same width, it is possible to increase the thickness of each wire and the spacing and pitch between wires. Accordingly, as the thickness of each wire increases, mechanical stability can increase, and as the interval between each wire increases, the possibility of short occurrence between the wires can be reduced.

Although the specification has been described as a structure in which the first electrode structure and the second electrode structure are stacked, the number of the stacked electrode structures is not particularly limited. In order to facilitate wire design, the number of stacking of the electrode structure may be appropriately adjusted.

Figure 47:
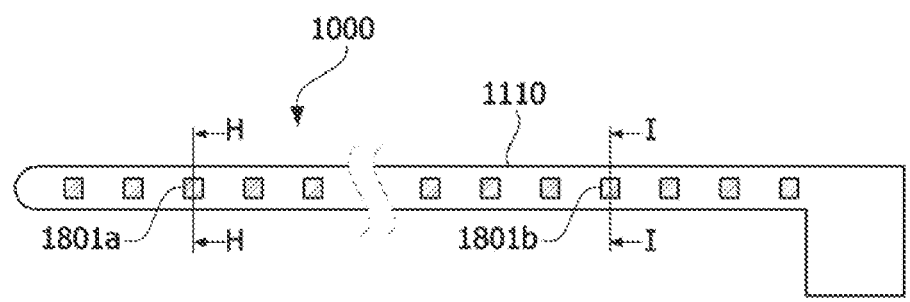
FIG. 47 is a view showing an electrode array according to a sixth embodiment.
Figure 48A:
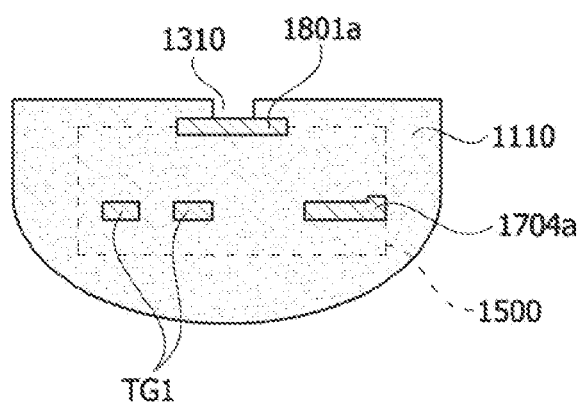
FIG. 48a is a cross-sectional view taken in H-H direction of FIG. 47.
Figure 48B:
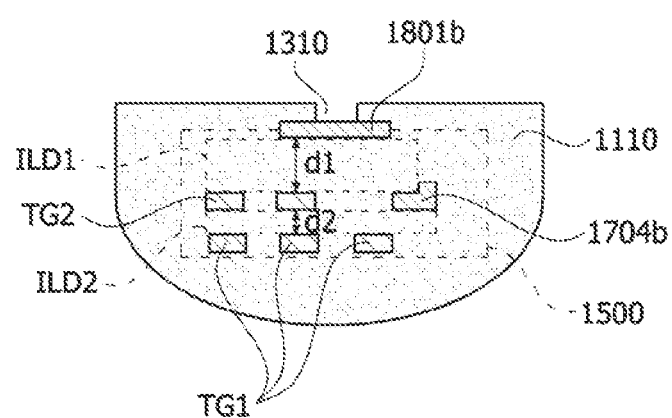
FIG. 48b is a cross-sectional view taken along I-I direction of FIG. 47.

FIG. 47 is a view showing an electrode array according to a sixth embodiment. FIG. 48*a* is a cross-sectional view taken in H-H direction of FIG. 47. FIG. 48*b* is a cross-sectional view taken along I-I direction of FIG. 47.

Referring to FIGS. 47 and 48*a*, in the electrode array 1000, the first contact electrode 1801*a* may form first to 16th channels, and the second contact electrode 1801*b* may form 17th to 32nd channels. However, the number of contact electrodes may be variously adjusted as needed. The first contact electrode 1801a may be exposed to the outside through the electrode hole 1310 formed in the housing 1110.

Referring to FIG. 48b, the second contact electrode 1801b may be exposed through the electrode hole 1310 formed in the housing 1110. In this case, the second wire group TG2 may be disposed in a region between the second contact electrode 1801b and the first wire group TG1 in a cross-section of the region where the second contact electrode 1801b is disposed. In this case, the cross-sections of the first contact electrode 1801a and the first connection wire 1704a may not be observed.

A first insulation region ILD1 may be formed between the second contact electrode 1801b and the second wire group TG2, and a second insulation region ILD2 may be formed between the second wire group TG2 and the first wire group TG1. In this case, the thickness of the first insulation region ILD1 may be thicker than the thickness of the second insulation region ILD2. Also, the vertical distance d1 between the second contact electrode 1801b and the second wire group TG2 may be greater than the vertical distance d2 between the second wire group TG2 and the first wire group TG1.

This is because the first insulation region ILD1 is formed by folding the second insulation layer on the second contact electrode 1801b and the second insulation layer on the second wire group TG2, while the second insulating region ILD2 has the thickness of the first insulation layer formed on the first wire group TG1.

However, the embodiment is not limited thereto, and the thicknesses of the first insulation region ILD1 and the second insulation region ILD2 may become the same or the thickness of the second insulation region ILD2 may be thicker by additionally forming an insulation layer for bonding between the insulation layers.

In addition, although not shown, the first pad part electrically connected to the first wire group TG1 and the second pad part electrically connected to the second wire group TG2 may be included at the end of the electrode array. The first pad part and the second pad part may be disposed on the same plane to facilitate electrical connection with the circuit. Here, being on the same plane may mean being disposed at the same height from a reference plane. However, the embodiment is not limited thereto, and the first pad part and the second pad part may be disposed on different planes.

In the above, the embodiment has been mainly described, but this is only an example and does not limit the present invention, and those of ordinary skill in the art to which the present invention pertains will appreciate that various modifications and applications not exemplified above are possible without departing from the essential characteristics of the present embodiment. For example, each component specifically shown in the embodiment can be implemented by modification. And the differences related to such modifications and applications should be construed as being included in the scope of the present invention defined in the appended claims.

What is claimed is:

1. An electrode array comprising:
    a housing;
    a plurality of first contact electrodes exposed to an outside of the housing;
    a plurality of second contact electrodes exposed to the outside of the housing;
    a first wire group disposed inside the housing and electrically connected to the first contact electrodes; and
    a second wire group disposed inside the housing and electrically connected to the second contact electrodes,
    wherein wires of the first wire group are extended in a first direction and spaced from each other in a second direction which is perpendicular to the first direction,
    wherein the plurality of first contact electrodes and the first wire group are disposed on different planes in a third direction which is perpendicular to the first direction and the second direction within the housing,
    wherein the second wire group is disposed on a different plane from the first wire group in the third direction, and
    wherein the plurality of first contact electrode and the plurality of second contact electrodes are disposed on a same plane in the third direction.

2. The electrode array according to claim 1, wherein the second wire group is disposed in a region between the second contact electrodes and the first wire group.

3. The electrode array according to claim 1, wherein a distance between the first contact electrodes and the first wire group is greater than a distance between the second contact electrodes and the second wire group.

4. The electrode array according to claim 1, further comprising:
    a plurality of first connection wires that electrically connects the first wire group and the plurality of first contact electrodes; and
    a plurality of second connection wires that electrically connects the second wire group and the plurality of second contact electrodes.

5. The electrode array according to claim 4, wherein the plurality of first connection wires is bent to electrically connect the first wire group and the plurality of first contact electrodes,
    the plurality of second connection wires is bent to electrically connect the second wire group and the plurality of second contact electrodes.

6. The electrode array according to claim 5, further comprising
    a first insulation region between the second contact electrodes and the second wire group; and
    a second insulation region between the second wire group and the first wire group.

7. The electrode array according to claim 6, wherein a thickness of the first insulation region is greater than a thickness of the second insulation region.

8. The electrode array according to claim 6, wherein a vertical distance between the second contact electrodes and the second wire group is greater than a vertical distance between the second wire group and the first wire group.

9. The electrode array according to claim 1, further comprising a first pad part electrically connected to the first wire group and a second pad part electrically connected to the second wire group,
    wherein the first pad part and the second pad part are disposed on the same plane.

* * * * *